United States Patent
Khanwilkar et al.

(10) Patent No.: US 6,302,661 B1
(45) Date of Patent: Oct. 16, 2001

(54) ELECTROMAGNETICALLY SUSPENDED AND ROTATED CENTRIFUGAL PUMPING APPARATUS AND METHOD

(76) Inventors: Pratap S. Khanwilkar, 1651 E. Shadow Cove, Salt Lake City, UT (US) 84121; Paul E. Allaire, 805 Emerson Dr., Charlottesville, VA (US) 22901; Gill Brent Bearnson, 982 E. Jasper Cir., Salt Lake City, UT (US) 84106; Don B. Olsen, 8832 Blue Jay La., Salt Lake City, UT (US) 84121; Eric H. Maslen, 748 Reas Ford Rd., Earlysville, VA (US) 22903; James W. Long, 4461 S. Parkview Dr., Salt Lake City, UT (US) 84124

(*) Notice: Subject to any disclaimer, the term of this patent is extended or adjusted under 35 U.S.C. 154(b) by 0 days.

(21) Appl. No.: 09/459,146

(22) Filed: Dec. 10, 1999

Related U.S. Application Data

(63) Continuation-in-part of application No. 08/850,156, filed on May 2, 1997, now abandoned.
(60) Provisional application No. 60/016,857, filed on May 3, 1996.

(51) Int. Cl.[7] .................................................. F04B 17/00
(52) U.S. Cl. ..................... 417/423.7; 417/420; 417/356; 417/423.12; 417/423.14; 415/900
(58) Field of Search ........................ 417/423.7, 423.12, 417/423.14, 420, 356; 415/900, 58.2, 58.3, 58.4, 57.3, 57.4; 604/151

(56) References Cited

U.S. PATENT DOCUMENTS

| | | | |
|---|---|---|---|
| 3,647,324 | * 3/1972 | Rafferty et al. | 417/420 |
| 4,135,253 | 1/1979 | Reich et al. | 417/420 |
| 4,589,822 | 5/1986 | Clausen et al. . | |
| 4,688,998 | 8/1987 | Olsen et al. | 417/356 |
| 4,880,362 | 11/1989 | Laing et al. . | |
| 4,944,748 | * 7/1990 | Bramm et al. | 417/356 |
| 5,017,103 | 5/1991 | Dahl | 417/420 |
| 5,044,897 | 9/1991 | Dorman | 417/423.7 |
| 5,112,202 | 5/1992 | Oshima et al. | 417/423.7 |
| 5,195,877 | 3/1993 | Kletschka | 417/356 |
| 5,350,283 | * 9/1994 | Nakazeki et al. | 417/423.7 |
| 5,470,208 | 11/1995 | Kletschka | 417/356 |
| 5,507,629 | 4/1996 | Jarvik . | |
| 5,658,136 | * 8/1997 | Mendler | 417/420 |
| 5,685,700 | 11/1997 | Izraelev | 417/423.7 |
| 5,725,357 | 3/1998 | Nakazeki et al. | 417/423.12 |
| 6,015,272 | * 1/2000 | Antaki et al. | 417/356 |
| 6,074,180 | * 6/2000 | Khanwilkar et al. | 417/356 |

FOREIGN PATENT DOCUMENTS

| | | | |
|---|---|---|---|
| 4-148095 | 5/1992 | (JP) | 417/423.7 |

\* cited by examiner

Primary Examiner—Charles G. Freay
Assistant Examiner—Cheryl J. Tyler

(57) ABSTRACT

An apparatus and method for a centrifugal pump for pumping sensitive biological fluids which includes (i) an integral impeller and rotor which is electromagnetically supported and rotated, (ii) a pump housing and arcuate passages for fluid flow and containment, (iii) a brushless driving motor embedded and integral with the pump housing, (iv) a power supply, and (v) specific electronic sensing and control algorithms—all fitly joined together to provide efficient, durable and low maintenance pump operation. A specially designed impeller and pump housing provide the mechanism for transport and delivery of fluid through the pump to a pump output port with reduced fluid turbulence.

24 Claims, 19 Drawing Sheets

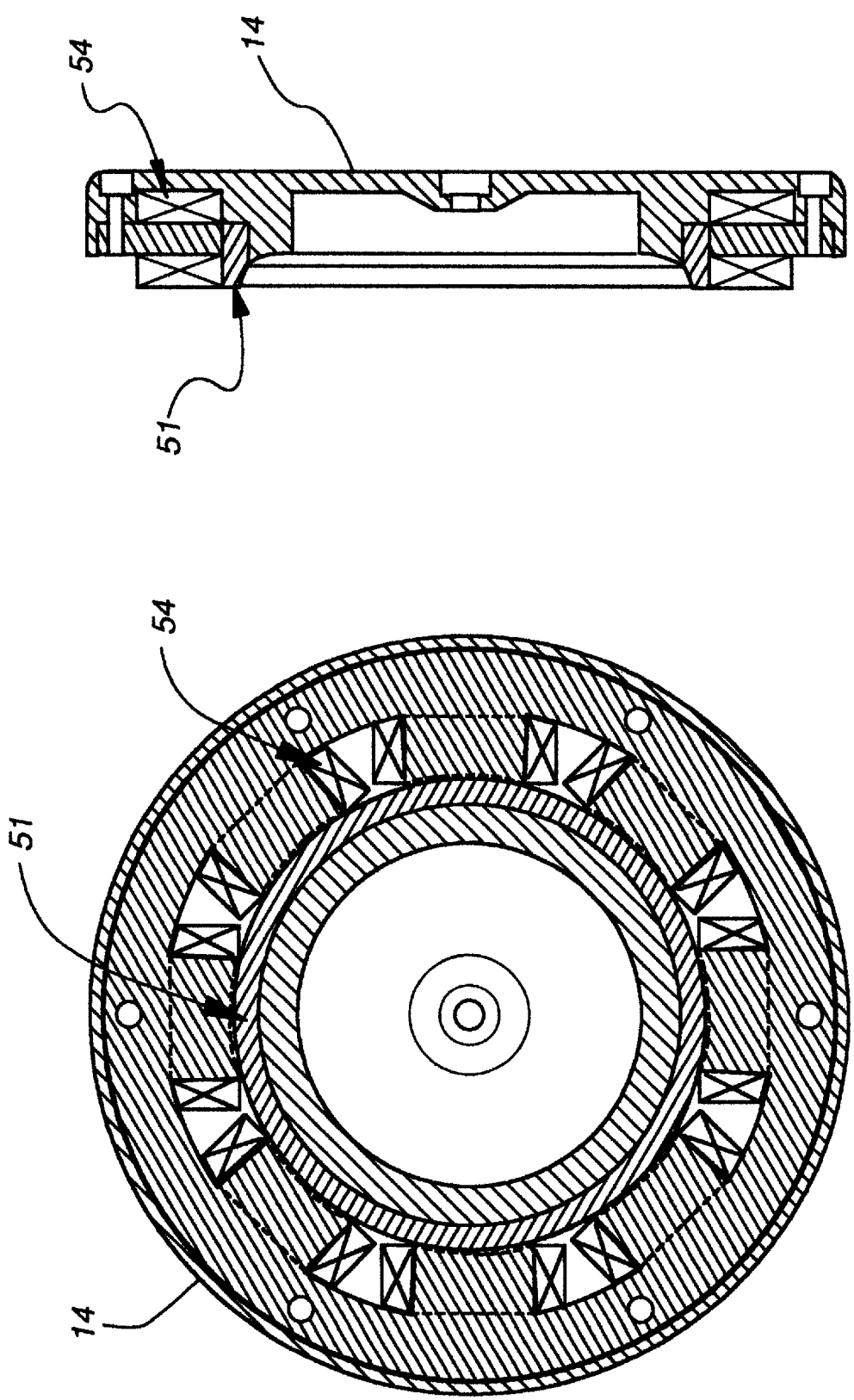

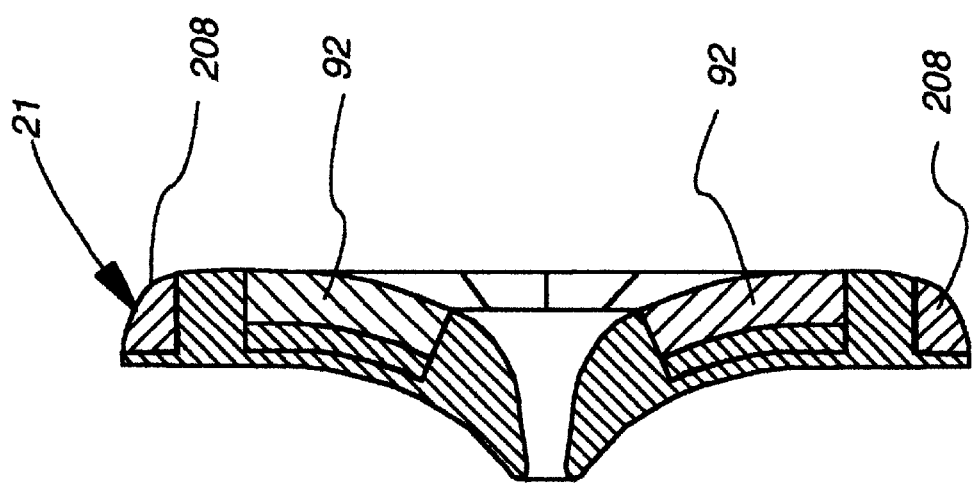
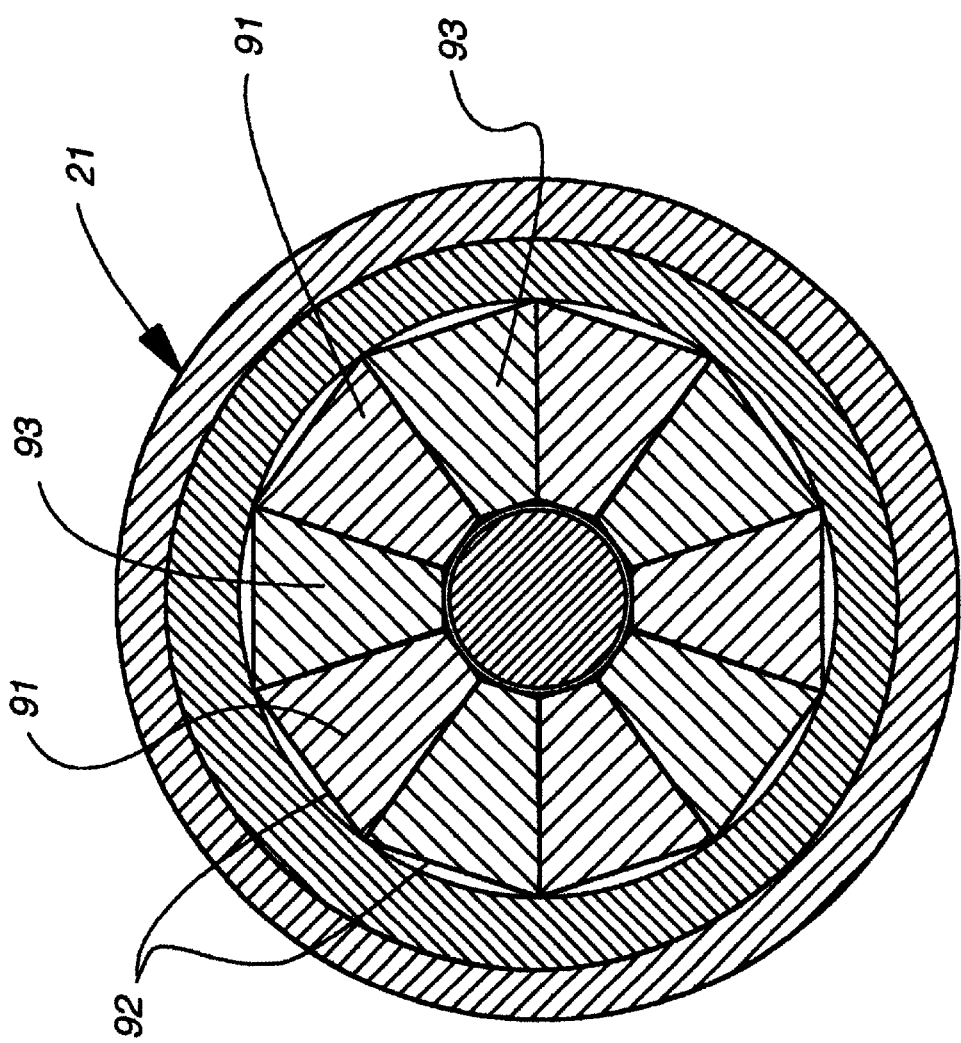
Fig. 7B
Fig. 7A

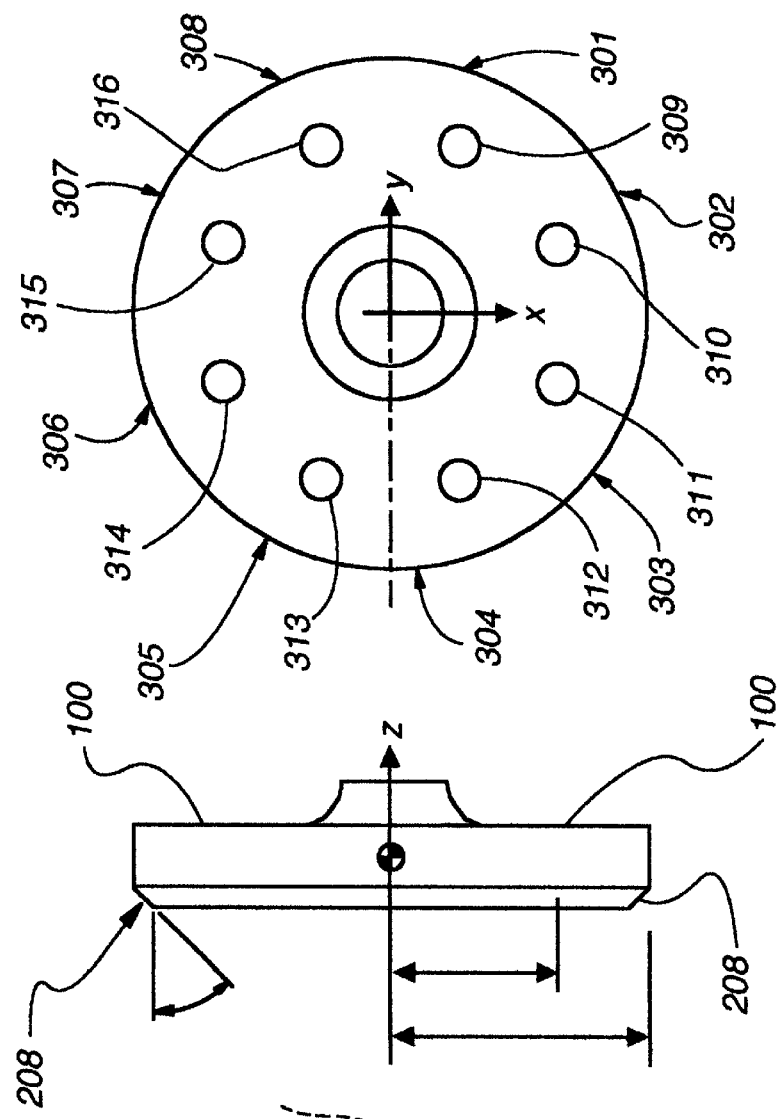
*Fig. 15A*
*Fig. 15B*
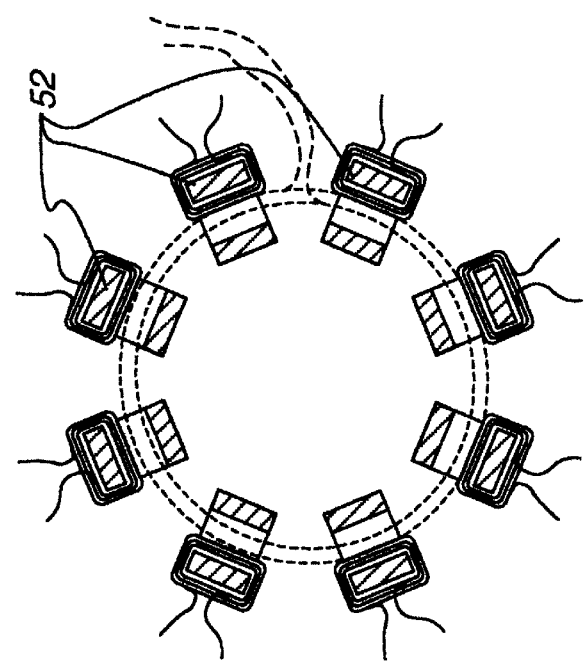
*Fig. 14*

ELECTROMAGNETICALLY SUSPENDED AND ROTATED CENTRIFUGAL PUMPING APPARATUS AND METHOD

This is a continuation-in-part application of application Ser. No. 08/850,156, filed on May 2, 1997 now abandoned, which is a continuation-in-part of copending provisional application Ser. No. 60/016,857, filed on May 3, 1996.

BACKGROUND OF THE INVENTION

1. Field of the Invention

This invention relates to magnetically supported and rotated rotors and, more particularly, to a centrifugal pumping apparatus and method whose disk-like impeller is electromagnetically suspended and rotated in a contact-free manner, the rotation speed of the impeller being controlled and changed electronically by fluid pressure and impeller positioning algorithms.

2. The Background Art

Historically, fluid pumps are of many and varied types and configurations, all performing essentially the same end result, namely, to provide fluid movement from one point to another. All pumps have a similar characteristic in that fluid is drawn into the pump through a vessel or pipe by a vacuum created by pump operation. In addition to the primary force of vacuum, secondary forces such as gravity, impeller inertia, or existing pipe/vessel fluid pressures also have an effect on fluid flow. Operation of the pumping mechanism creates a fluid pressure and/or fluid velocity which subsequently creates the vacuum that draws fluid into the pump through a pump inlet port. Fluid from the inlet port is transported throughout the pump by the pump mechanism which subsequently directs fluid to a pump outlet port.

Fluid pump configurations vary mostly by adaptation to function. For example, lift and force pumps utilize a reciprocating motion to displace fluid, whereas vacuum pumps create a vacuum that is used to displace fluid. Rotating axial-flow pumps utilize propeller-like blades attached to a rotating shaft to accomplish the displacement of fluid. Jet pumps utilize a steam-jet ejector which enters a narrow chamber inside the pump and creates a low-pressure area that correspondingly creates a suction that draws the fluid into the chamber from an inlet port. Although, other pump types could be specified, more specific reference will be made hereafter to fluid pumps for a sensitive fluid such as blood which are more easily adaptable to environments where size and geometry of the pump are critical.

The rotating centrifugal pump is, by nature, more tightly configured and readily adaptable to pumping of sensitive fluids. Blood flow pumps have relatively low flow rate performance characteristics compared to many ordinary industrial applications yet have significant pressure rise requirements. Centrifugal pumps are well suited to such applications rather than axial flow pumps or other designs. This leads to the use of a centrifugal pump design for the preferred embodiment of this invention. The pump includes several ribs or vanes mounted to an impeller whose rotational force impels fluid toward the outside of the rotor by centrifugal force. Centrifugal pumps traditionally possess a shaft-mounted impeller immersed in the fluid, where the shaft extends through a seal and bearing apparatus to a drive mechanism. Revolving vanes of the impeller create a partial vacuum near the center of the axis of rotation which correspondingly draws in fluid through the intake opening of the pump. A smooth pump volute is located in the pump stationary component to assure the smooth flow of pumped fluid from the exit of the impeller to the pump exit passage. The volute accumulates the pump flow as it exits the pump impeller and performs the function of increasing the fluid pressure (head) by converting fluid kinetic energy (velocity) to potential energy (pressure or head). Although centrifugal pumps do not require valves for movement of fluid, pump geometry must be such that fluid drawn in through the input opening will continue through the pump mechanism and on to the outlet port without significant internal fluid leakage or inefficiencies.

These prior art pumps are known to have problems. For example, it is well documented that shaft seals as configured in conventional centrifugal pumps are notoriously susceptible to wear, failure, and even attack by certain fluids, thus resulting in leakage problems. It is also well known that pumps for some fluids require more careful design consideration and require specific pumping techniques in order to avoid fluid damage, contamination, and other undesirable conditions. For example, fluids such as corrosive fluids (acids or caustics) or sensitive fluids such as blood, require special consideration such that seals do not leak and thereby lose integrity of the fluid. Pumping of sensitive fluids, such as blood, by continuous flow pumps requires highly reliable and non-damaging bearings to support the rotating impeller. Prior art pumps have very significant problems with bearings needed to support the impeller as it rotates. Ball and other rolling element bearings can only be employed if isolated from the sensitive fluid (blood) by shaft seals and lubricated with non-body fluids. In this situation, all of the sealing problems indicated above apply. If the conventional ball or other rolling element bearings employ the sensitive fluid as a lubricant, the sensitive fluid living properties, such as red blood cells in blood, are destroyed in a short period of time due to being ground between the rolling components in the bearings. Thrust and radial fluid film bearings, lubricated with the sensitive fluid, have been employed in some prior art pumps. These have been subject to poor performance and/or many failures due to seizure of the rotating component in the stationary component, production of thrombosis (clotting), damage to the sensitive fluid due to hemolysis (high shear), and other problems. Fluid film bearings also do not provide any information on the instantaneous pump pressures and flow rates that can be employed for speed control of the motor to match physiological needs to future pump performance. Conventional ball bearings and fluid film 103 thrust and radial bearings do not have the long term reliability required for pumps in which fluid stasis and high fluid shear stress must be avoided, such as blood pumps. Furthermore, ball bearings have a limited life when employed in the pumping of sensitive fluids and often must be lubricated by an external lubricating fluid which requires seals to contain the lubricating fluid. Transport and containment of lubricating fluid for bearings increases the overall size of the pump housing as well as increasing complexity of operation due to extra vessels and mechanisms used to deliver and cool lubricating fluid, thereby making pump apparatus non-implantable if used to replace natural heart functions. Therefore, the relatively short life of fluid pumps with shafts and conventional bearings makes them unsuitable for implanting in body cavities for the long term replacement of natural heart functions.

Furthermore, pumping of blood involves specific known hazards typically associated with shaft seals for impeller-type blood pumps due to pockets of fluid being susceptible to stagnation and excessive heat. Further still, pumping sensitive fluids, such as blood, requires careful consideration of geometry of impeller vanes and pump housing. Excessive mechanical working and heating of blood causes blood components to breakdown by hemolysis and protein denaturization, which leads to blood coagulation and thrombosis.

Avoidance of blood damaging effects of pump operation is best accomplished by natural heart function. The natural heart has two basic functions, each side performing a different pumping function. The right side of the natural heart receives blood from the body and pumps it to the lungs, whereas the left side of the natural heart collects blood from the lungs and pumps it to the body. The beating of the natural heart, in combination with heart valves, provides blood pumping action in a pulsatile, remarkably smooth and flowing manner. Blood flow (cardiac output) of the natural heart is primarily regulated by venous return, otherwise known as pump preload. However, due to diseases or accident, natural heart functions can be partially or totally lost. Mechanical apparatus developed to replace natural heart functions historically ranged in size from extremely large in the earliest heart-lung or pump oxygenator apparatus to more recent apparatus whose size and function more closely resembles that of the natural heart.

In addition to total heart replacement, development of other mechanical apparatus focuses on replacement of a portion of the function of the natural heart, such as a ventricular assist device that aids a failing left ventricle weakened by disease or other damage. A primary consideration for natural heart function replacement, whether partial or total, is that blood must be pumped throughout the entire apparatus in a gentle, low thermal, and non-destructive manner. For example, if a pump impeller supported by mechanical bearings comes in contact with blood, relative movement between parts of the bearings results in excessive mechanical working of the blood which causes blood cells to rupture, resulting in hemolysis. Another mechanical effect that can injure blood is formation of regions within the pump where blood is semi-stagnant or where blood will eddy without sufficient blood exchange, thereby creating the equivalent to blood stagnation. The result of blood stagnation often is coagulation of the blood (thrombosis), which correspondingly causes blood to cease to flow at all. Yet another effect that can injure blood is excessive heating due to friction of a sidewall of the pump or other pumping mechanisms as blood passes through the pump. Specifically, side wall friction caused by abrupt angular changes of internal pump geometry requires blood to follow harsh changes of direction and thereby creates excessive mechanical working of blood which causes blood cell rupture or activation of blood platelets and corresponding hemolysis and thrombosis. Yet another effect that can injure blood is caused by inefficient pump operation whereby a large part of the energy supplied to the pump appears as heat discharged into the blood which damages blood by overheating and coagulation. Notably, because blood albumen begins to denature at 42 degrees Centigrade, inefficiencies in pump operation which result in overheating of the blood will cause a very serious and life threatening condition.

The before mentioned conditions of stagnation, harsh pump geometry, turbulence and/or heating will activate blood platelets and/or damage oxygen-carrying red blood cells. Damage to blood starts a chain reaction that forms a thrombus with potential to block blood vessels, starving the tissues it nourishes, and leading to a serious, life threatening condition. Numerous attempts to avoid the foregoing problems associated with pumping blood have been made using flexible diaphragms and collapsible tubing in roller pumps. However, the continual flexing of the diaphragm and/or tubing material is known to change the blood-contacting properties of the material resulting in material fatigue, dislodged fragments of the internal wall of the flexible material, and emboli passed into the bloodstream by the fragments.

In addition to the above mentioned conditional requirements for pumping blood, the rate of impeller rotation has a significant effect on stability and structure of sensitive vessels. Impeller rotational operation that is not regulated by pump preload pressure will cause atrial suction in sensitive vessels just prior to the pump inlet port, wherein blood vessels collapse when impeller rotation exceeds blood vessel wall rigidity. Prior art pumping apparatus has not provided adequate integration of controls to insure that rapid adjustments to impeller rotational speed does not have a negative effect.

Kletschka '005 (U.S. Pat. No. 5,055,005) discloses a fluid pump levitated by opposing fluid. Stabilization of impeller by opposing fluid alone is not sufficient to maintain impeller in precise position within pump housing, as well as high pressure fluid jets subject blood to the before mentioned blood coagulation caused by mechanical working of blood.

Kletschka '877 (U.S. Pat. No. 5,195,877) discloses a fluid pump with a magnetically levitated impeller utilizing a rigidly mounted shaft surrounded by a magnetically levitated rotor which serves as an impeller for fluid. The shaft of this invention introduces a requirement for a hydraulic bearing and seal at the juncture of the shaft and the rotating impeller which subjects blood, or other sensitive fluids, to thermal and stagnation conditions at the region of the bearing.

For more than 25 years, those skilled in the art have studied pumps that are used as total artificial hearts and experimentally implanted in animals. These studies have provided useful feedback of the relative effectiveness of blood pumping apparatus. These pumps can be categorized as producing pulsatile or non-pulsatile flows. The pumps producing pulsatile fluid motion (positive displacement pumps) more closely resemble fluid motion as provided by the natural heart. Information to date has not yet determined if pulsatile fluid movement is needed to provide a necessary physiological benefit, or if the pulsatile fluid motion is primarily due to the non-rotary nature of heart muscle. Most pulsatile pumps universally require valves (mechanical or tissue) with inherent mechanical problems and limitations.

Although valve systems are not required in prior art non-pulsatile pumps, the non-pulsatile pumps require rotating shafts passing through various bearings and seals. These shafts create inherent problems of blood stagnation, contamination and undesirable thermal conditions, thereby making long term use of the pumps as a replacement for natural heart function unfeasible. Most early prior art rotating non-pulsatile systems were installed outside of the body for short-term cardiac assistance and experienced a moderate amount of success.

One blood pumping apparatus is the total artificial heart. The total artificial heart has been used in five patients as a permanent replacement for pathological, irreparable ventricles; and in 300 patients as a temporary bridge to cardiac transplantation. The longest support on the total artificial heart has been 795 days. Other blood pumping apparatus, e.g., ventricular assist devices, have been used in patients unweanable from cardiopulmonary bypass during cardiac surgery or those whose one ventricle only has failed. The most common mechanical replacement of natural heart function is a temporary bridge to cardiac transplantation by a ventricular assist device with over 1250 patients receiving such temporary ventricular assist apparatus.

Historically, blood pumping apparatus have presented many problems. For example, the pumping mechanism of reciprocating (diaphragm) total artificial hearts has been energized with gases (pneumatic systems), fluid (hydraulic systems), electricity (motors, solenoids, etc.), and skeletal muscles. The energy sources and associated convertor systems possess additional components that increase complexity of the total system and thereby contribute to overall unreliability. Also, the size of prior art systems for total artificial hearts is very restrictive to patient mobility and not conducive to quality of life of the recipient. Another constraining factor not fully met by prior art apparatus is that the excessive size and complexity of energy conversion systems, as well as overall pump design exceeds the available anatomical space. Furthermore, most of these prior art reciprocating systems exhibit excessively high (i) noise characteristics, (ii) vibration, and (iii) recoil (thrust) levels.

Many of the problems of the prior art rotating pumps have been addressed by those skilled in the art through pump adaptation with capability to meet the above mentioned requirements for pumping sensitive fluids (such as blood). These pump adaptations can be accomplished by support of the impeller through electromagnets located on the impeller and the housing such that the impeller can be rotated without shafts, seals or lubricating systems. Permanent magnets without some form of additional support cannot entirely suspend an object, such as an impeller, but require additional adjustable support or force in some axis to achieve stabilized suspension. This is based on Eamshaw's theorem which indicates that suspension systems comprised solely of permanent magnets will not be stable. However, actively controlled electromagnets can be used to stabilize and support an object with respect to all degrees of freedom of movement. Therefore, electromagnets, through calculated positioning, can provide stable suspension of an object (or impeller in the case of the centrifugal fluid pump). The only expenditure of energy in magnetically supported impellers is electromagnetic energy utilized for stabilizing and rotating the impeller. Electromagnets for impeller suspension and rotation create stable and efficient pump operation.

Within the past decade, prior art patents have disclosed magnetically suspended and rotated rotors which have exhibited a degree of success. These prior art configurations utilize partial magnetic suspension to reduce hazards to blood. Although magnetically suspended prior art devices successfully reduce some of the friction hazard of the rotary shaft, the prior art devices are still impractical for implantation in total heart replacement due to size, complexity, and less than optimal impeller positioning, position sensing, and speed control. The excessive size and difficulty in maintaining precise impeller positioning and speed of these prior art inventions is due mostly to geometric configuration of the impeller, which is cylindrical, spherical, or otherwise mostly three dimensional in nature.

In view of the foregoing, it would be a significant advancement in the art to provide improvements in magnetically suspended and rotated centrifugal pumping apparatus to thereby allow for reduced size and increased accuracy in impeller positioning and speed controls. It would also be an advancement in the art to provide a centrifugal pumping apparatus that would be free of shafts, rolling element or fluid film bearings, mechanical seals, or physical proximity sensors, thereby allowing for a fully integrated pump design without mechanical contact, wear, failure due to seizing up of fluid bearings, and generation of thrombosis or shear damage. An even further advancement in the art would be to provide a centrifugal pumping apparatus with geometry of impeller and pump housing such as would provide efficient and low-turbulence transport of fluid throughout pump mechanisms including the pump output port. Further still, it would be an advancement in the art to provide a versatile centrifugal pumping apparatus that could operate in either pulsatile or non-pulsatile mode.

OBJECTS AND SUMMARY OF THE INVENTION

It is therefore a primary object of the present invention to provide improvements in rotating centrifugal fluid pumps for sensitive fluids.

It is another object of the present invention to provide improvements in fluid pumps using efficient non-contact electromagnetic bearings and an efficient motor.

It is also an object of the present invention to provide a centrifugal pumping apparatus of relatively compact size to enable anatomical implantation.

It is a further object of the present invention to provide a centrifugal pumping apparatus and method to provide a long product life and which requires minimal maintenance.

It is an additional object of the present invention to provide improvements in centrifugal fluid pumps which are used for partial or total heart function replacement.

It is still another object of the present invention to provide a centrifugal pumping apparatus and method whose pump design geometry provides efficient and low-turbulence transport and output of sensitive fluid throughout the pump, including low-turbulence output just beyond the outlet port.

It is yet another object of the present invention to provide a centrifugal pumping apparatus and method whereby fluid pressure and output fluid volume are controlled and changed electronically via specific fluid pressure and positioning algorithms.

It is another object of the present invention to provide a centrifugal pumping apparatus and method that is capable of operation in either pulsatile or non-pulsatile mode.

It is yet another object of the present invention to provide a centrifugal pumping apparatus and method that is adaptable as either a ventricular assist device or paired to provide a total heart replacement.

The above objects and others not specifically recited are realized through an apparatus and method for a centrifugal fluid pump for pumping sensitive biological fluids, which includes (i) an integral impeller and rotor which is entirely supported by integral electromagnetic bearings and rotated by an integral motor, (ii) a pump housing and arcuate passages for fluid flow and containment, (iii) a brushless driving motor embedded and integral with the pump housing, (iv) a power supply, and (v) specific electronic sensing of impeller position, velocity or acceleration using a self-sensing method and physiological control algorithm for motor speed and pump performance based upon input from the electromagnetic bearing currents and motor back emf—all fitly jointed together to provide efficient, durable and low maintenance pump operation. A specially designed impeller and pump housing provide the mechanism for transport and delivery of fluid through the pump to a pump output port with reduced fluid turbulence.

These and other objects and features of the present invention will become readily apparent from the following description in which preferred and other embodiments of the invention have been set forth in conjunction with the accompanying drawings and appended claims.

BRIEF DESCRIPTION OF THE DRAWINGS

The above and other objects, features and advantages of the invention will become apparent from a consideration of the following detailed description presented in connection with the accompanying drawings in which:

FIG. 4A is a plane view of a cross-section taken through section 4A of FIG. 3.

FIG. 4B is a partial view of the cross-section of FIG. 3.

FIG. 7A is a plane view of a cross-section taken through section 7A of FIG. 3.

FIG. 7B is a partial view of the cross-section of FIG. 3.

FIG. 14 depicts a circular array of eight horseshoe electromagnets used to form a thrust/moment bearing configuration at a face of an impeller;

FIG. 15A depicts a planar view of a circular array of four horseshoe electromagnets used to form a radial/thrust bearing configuration at a stator in the pump;

FIG. 15B depicts a cross-sectional view of a circular array of four horseshoe electromagnets used to form a radial/thrust bearing configuration at a stator in the pump;

DETAILED DESCRIPTION

Figure 1:
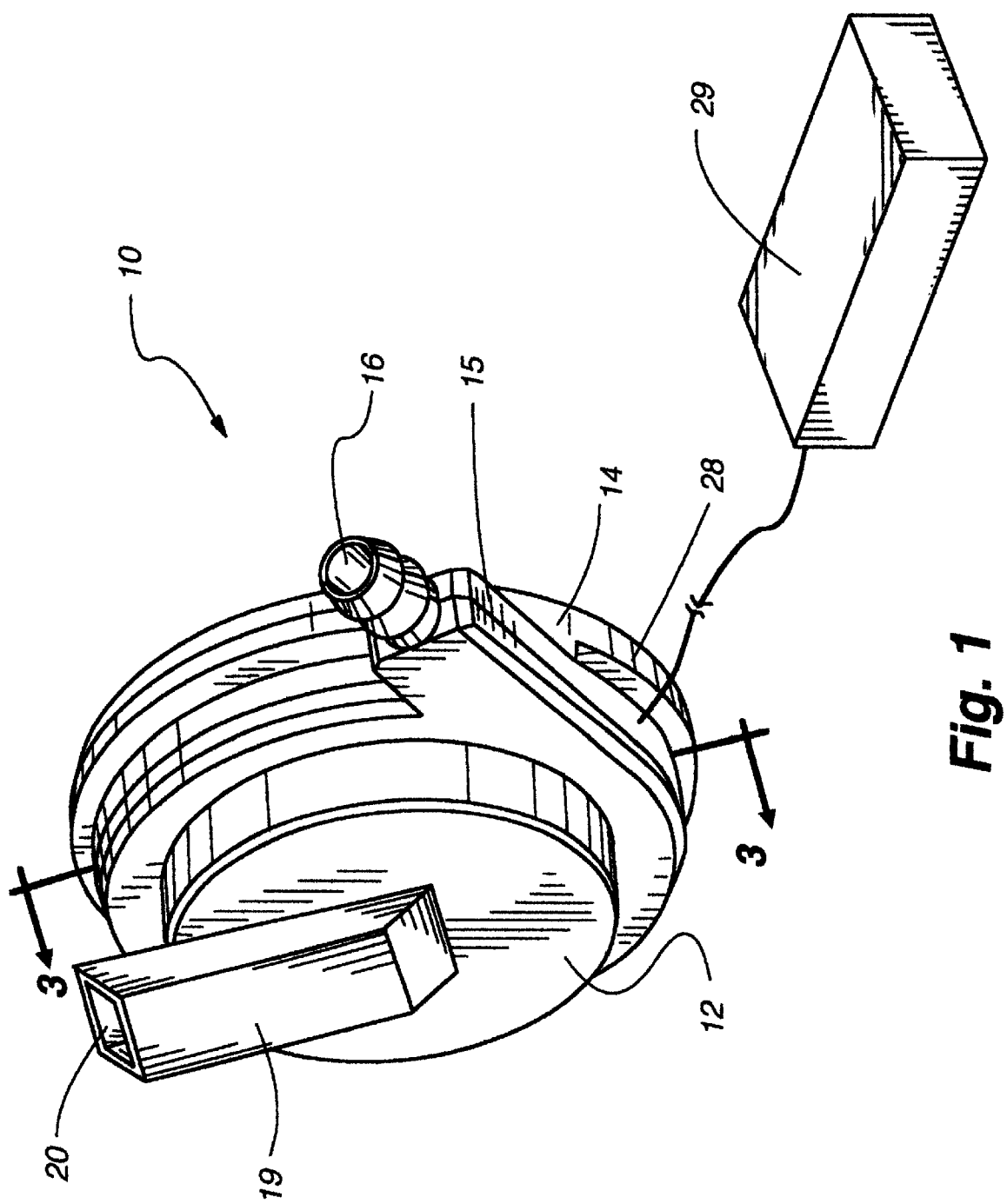
FIG. 1 is a perspective view of the magnetically supported and rotated pumping apparatus of this invention.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the appended claims.

General Discussion

The underlying rationale for a rotating centrifugal pump with an impeller, fully supported in electromagnetic bearings and rotated by an electric motor, is to prevent blood or other sensitive fluid damage due to conditions of (1) excessive heat, (2) stagnation, and (3) coagulation or fluid instability caused by turbulence or mechanical working of fluid due to harsh pump design. Furthermore, the apparatus size of this invention is capable of fitting into available anatomical space if used for total natural heart replacement or ventricular assistance.

To be suitable as a blood pump, the pump must be able to adequately meet physiological perfusion needs of a ventricular or biventricular assist device for total heart replacement. As a total heart replacement device, the pump must be of sufficiently small size and mass to be implantable within available anatomical space and not cause any negative effects on anatomy due to excessive apparatus weight. Furthermore, the disc-like shape of the impeller of this invention significantly reduces size and complexity of the pumping apparatus. The pumping apparatus of the invention can be used singularly as a ventricular assist device that assists or replaces partial heart function or a pair of devices can be combined to form a total heart mechanical replacement. The combined size of two devices in a total mechanical heart replacement is approximately the size of a natural heart, thereby enabling implantation within existing anatomical space.

The impeller of this invention is entirely suspended and enclosed within its pump housing, thereby providing contact-free operation between pump impeller and any other portion of the pump. The pump impeller is suspended in electromagnetic bearings. An electric motor rotates the pump impeller to perform the pumping function of fluid and provide adjustments to impeller positioning relative to pump housing. The notable absence of shafts, ball bearings, shaft seals or other sources of contamination make possible significantly extended product life of the pumping apparatus of this invention, thereby enabling long term natural heart replacement.

The pump impeller rotates about an axis and the term "axial direction" is employed here to denote the direction parallel to the axis of rotation of the pump impeller. The term "radial direction" is used here to denote directions perpendicular to the axial direction. The invention consists of electromagnetic bearings, comprising magnetic and other materials, activated by electrical currents in coils wound around the bearing magnetic components, which develop both axial and radial forces. A multiplicity of magnetic bearings, in a suitable configuration arranged around the impeller, is required to center the impeller during operation of the pump and to avoid contact between the rotating and stationary components. This non-contacting operation allows the bearings to operate without wear or friction losses.

Impeller position and rotational speed of this invention are controlled by specific algorithms which sense fluid pressure and the 6-axis location of pump impeller within pump housing, correspondingly making adjustments to rotational speed and/or impeller position to provide a fully integrated system of physiological control. Impeller rotational speed is adjusted to correspond to fluid pressure at pump preload pressure (inlet pressure) and/or exit pressure to match bodily needs for increased or decreased pump flow rate or pressure rise.

The geometric design of the pumping apparatus of this invention provides fluid movement throughout the entire pump mechanism in a smooth, non-turbulent, and low thermal manner. Impeller rotation causes fluid to move centrifugally by specially curved impeller vanes which emanate from the epicenter of the disc-like impeller and extend toward the outside of the impeller, and simultaneously create a partial vacuum at the region near the impeller's axis of rotation that draws additional fluid into the inlet port. Blood, or other sensitive fluid, does not stagnate at any location within the pumping apparatus due to return fluid flow along the side of the impeller which returns fluid to the impeller epicenter without flow interference from stagnation pockets, bearings or seals. Importantly, the geometry of the pump housing, the impeller vanes, the outlet port, and all other aspects of the pumping apparatus of this invention are such that sensitive fluids are protected from damage otherwise caused by stagnation, excessive heat, turbulence, and excessive mechanical working of the fluid. The fluid is transported throughout the entire pumping apparatus without harsh angular redirection to flow. The configuration of pump housing is designed with a spiral volute curve such that the same curve slope throughout the pump housing enables fluid to be transported within the pump housing with no net abrupt angular change of direction, nor corresponding net increase in thermal friction and energy loss due to friction from the pump side wall.

Another important feature of the pumping apparatus of this invention is the capability of operation in either pulsatile or non-pulsatile mode. Cyclic variance of impeller rotational speed will cause the pump to operate in a pulsatile mode, which more closely resembles pumping action by the natural heart, whereas uniform impeller rotational speed operates the pump in non-pulsatile mode. Operational mode change from pulsatile to non-pulsatile or vice versa is accomplished through changes to the pump operation settings, thereby avoiding trauma associated with replacing the total pumping apparatus when a change from either pulsatile or non-pulsatile is determined to be the preferred operation mode.

Preferred Embodiments

Referring now to FIG. 1, the magnetically suspended and rotated centrifugal pumping apparatus of this invention is shown generally as construct 10. Construct is configured with a first pump housing half 12 and a second pump housing half 14, together with hermetic seal 28, to form the confines for enclosure of the remainder of the pumping components, discussed in detail hereafter. An electronic controller 29 and batteries or other power source (not shown) are electrically connected to the construct 10, and are necessary for operation, as described in more detail hereafter. Construct 10 is configured with one or more pump inlet vessels, shown in FIG. 1 with one inlet vessel 19 as the preferred embodiment. Pump inlet vessel 19 is seamlessly formed and integral to first pump housing half 12 and includes an inlet throughbore 20 which provides containment for fluid entering pump construct 10. Fluid enters pump construct 10 via pump inlet vessel 19, which provides containment and delivery of fluid by inlet flow throughbore 20, to a region proximate to the axial center of pump construct 10. Outlet vessel 15 is located tangentially from the outside diameter of construct 10 and is formed by the combining of first pump housing half 12 and second pump housing half 14 with containment walls forming pump outlet throughbore 16 and sealed by hermetic seal 28.

Figure 2:
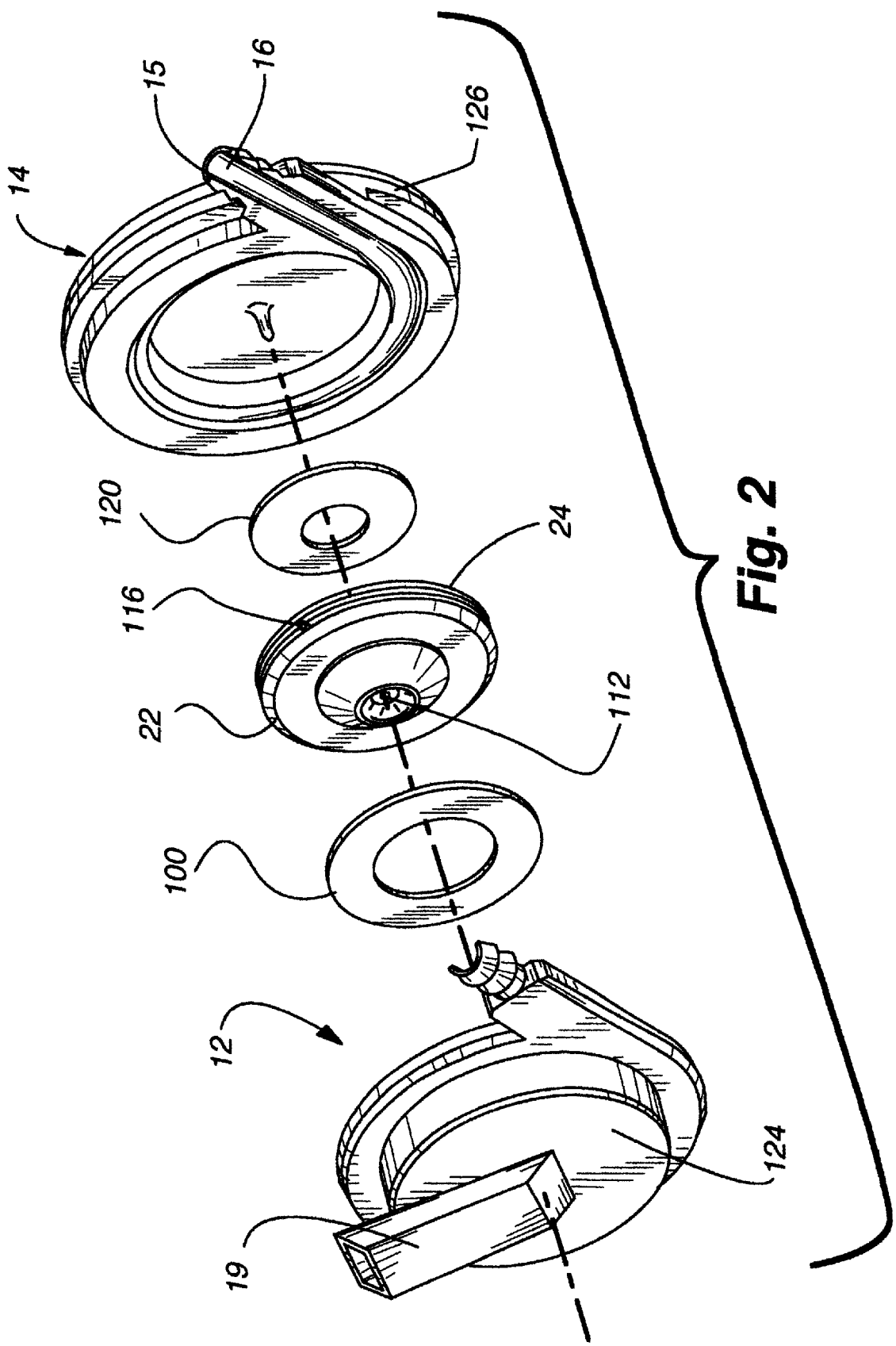
FIG. 2 illustrates an exploded side view of a pumping apparatus fully supported in electromagnetic bearings, and rotated by an electric motor of this invention.

FIG. 2 illustrates an exploded side view of the magnetically supported and rotated pumping apparatus of this invention. The exploded view shows the pump inlet 19, the first pump half 12, a bearing target 100, an impeller shroud 22, an impeller hub 24, an impeller inlet 112, an impeller vane 116, a motor rotor 120, the outlet vessel 15, and the pump outlet throughbore 16. Also shown in FIG. 2 is a combined axial thrust and moment bearing housing 124 and a combined radial and axial thrust bearing housing 126. Bearing target 100 is preferably formed of non-permanently magnetized magnetic material, such as soft iron. Other non-permanently magnetized magnetic materials, such as iron-cobalt alloys with similar properties, may also be used. The bearing targets and rotor control methodology are discussed in more detail below.

Figure 3:
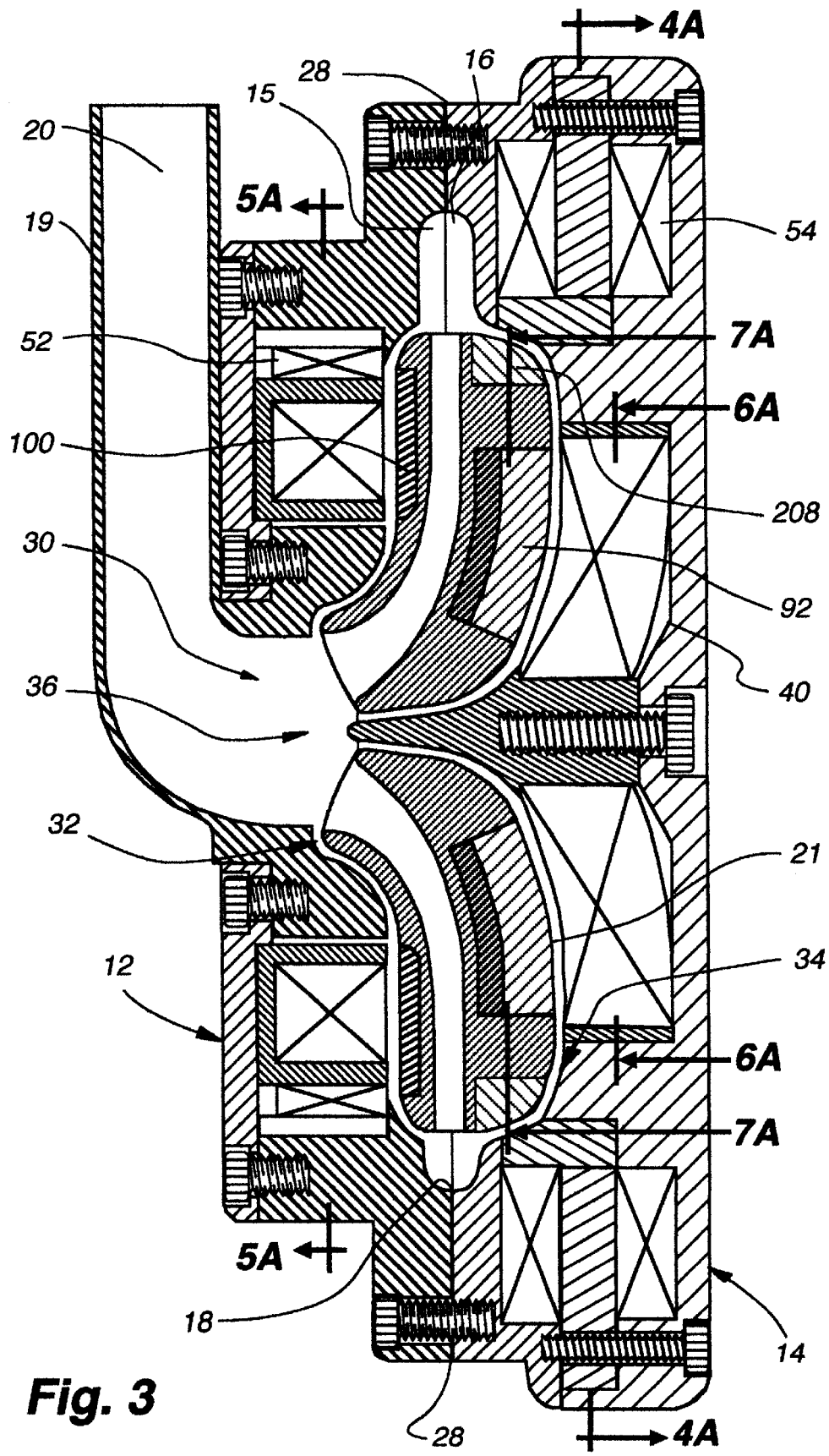
FIG. 3 is a cross-sectional view of FIG. 1 taken along line 3—3.

Referring to FIG. 3, spiral volute exit 18 is formed by the combination of first pump housing half 12 and second pump housing half 14, and sealed by hermetic seal 28. Importantly, the configuration of the logarithmic spiral volute exit 18 of this invention utilizes a spiral volute curve formation to eliminate abrupt or harsh changes of direction to fluid flow during transportation from impeller to outlet vessel 15, thereby avoiding damage to sensitive fluids as described herein before. The combination of first pump housing half 12 and second pump housing half 14, together with hermetic seal 28, also forms containment for internal impeller 21 and impeller chambers 27a, 27b, 27c, and 27d (see FIG. 9), discussed hereafter in detail. Fluid flows entirely around impeller 21 via first return flow chamber 32 and second return flow chamber 34.

FIG. 4A depicts a plane view of section 4A from FIG. 3. Section 4 is a portion of the second pump (or construct) 10 housing half 14. FIG. 4B depicts a cross-sectional portion of section 4 of the second pump housing half 14. Windings 54 in the structure are clearly visible and enable construction of this portion of the pump 10. Also shown in FIG. 4A and FIG. 4B is a conical pole face 51.

Figure 5A:
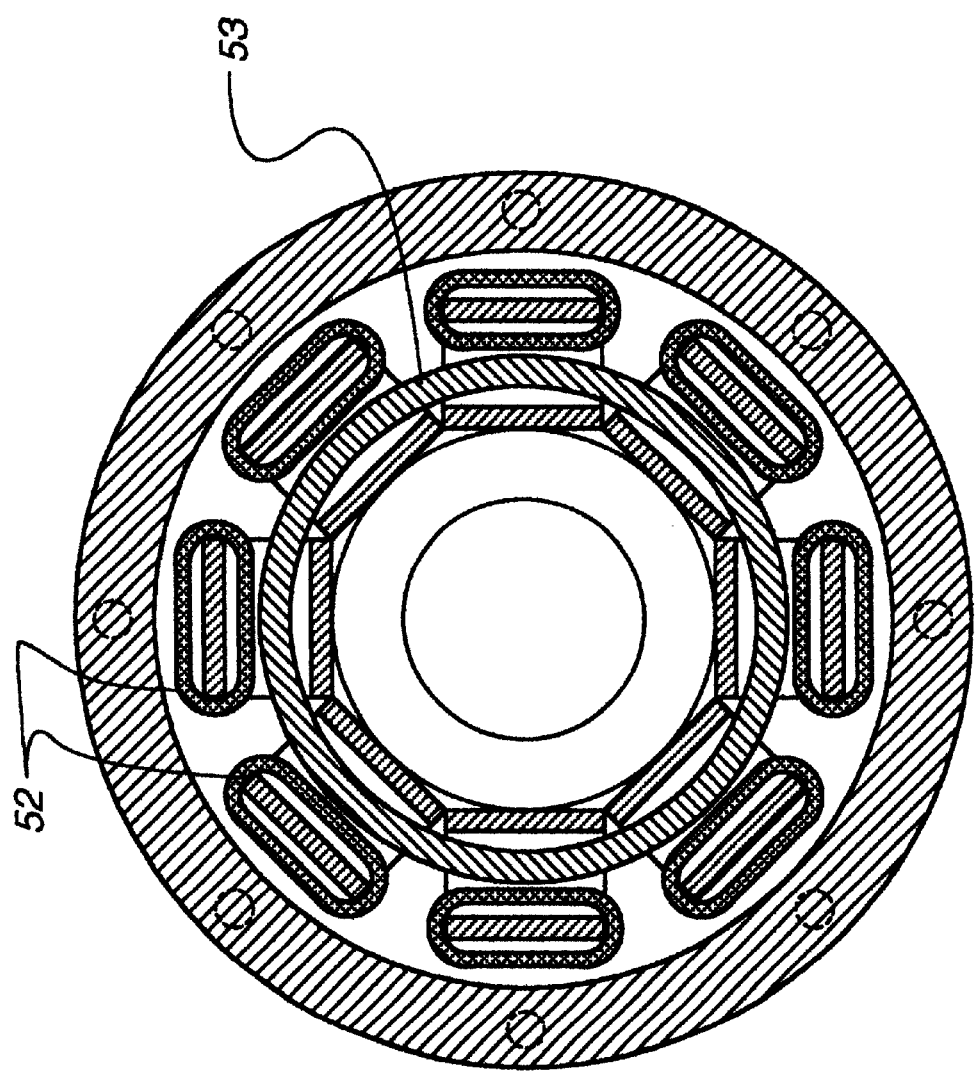
FIG. 5A is a plane view of a cross-section taken through section 5A of FIG. 3.
Figure 5B:
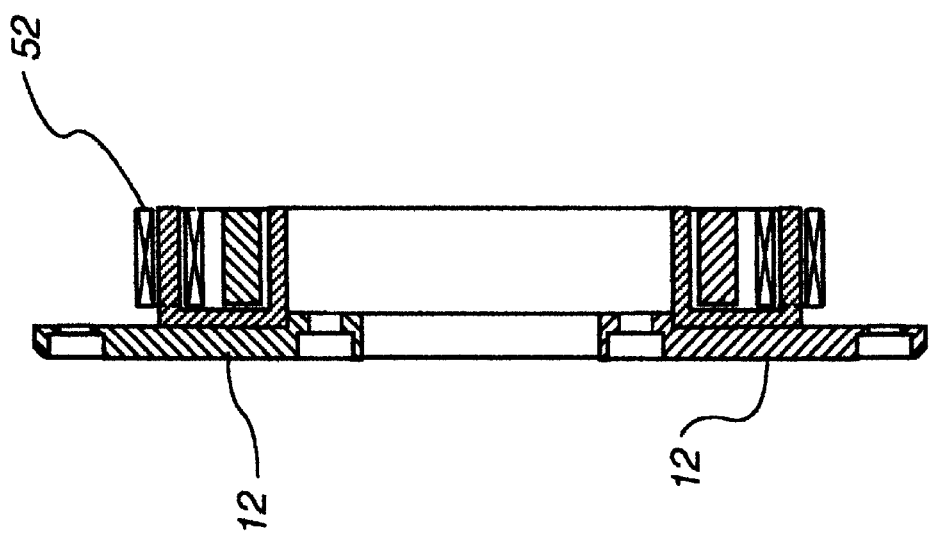
FIG. 5B is a partial view of the cross-section of FIG. 3.

FIGS. 5A and 5B similarly depict a portion of the pump 10, however, FIG. 5A shows a plane view of section 5A (see FIG. 3) of the first pump housing half 12 and FIG. 5B shows a cross-sectional view of section 5A of FIG. 3. Windings (or control coils) 52 and a bias coil 53 are shown to enable construction of the pump 10 by those skilled in the art.

Figure 6B:
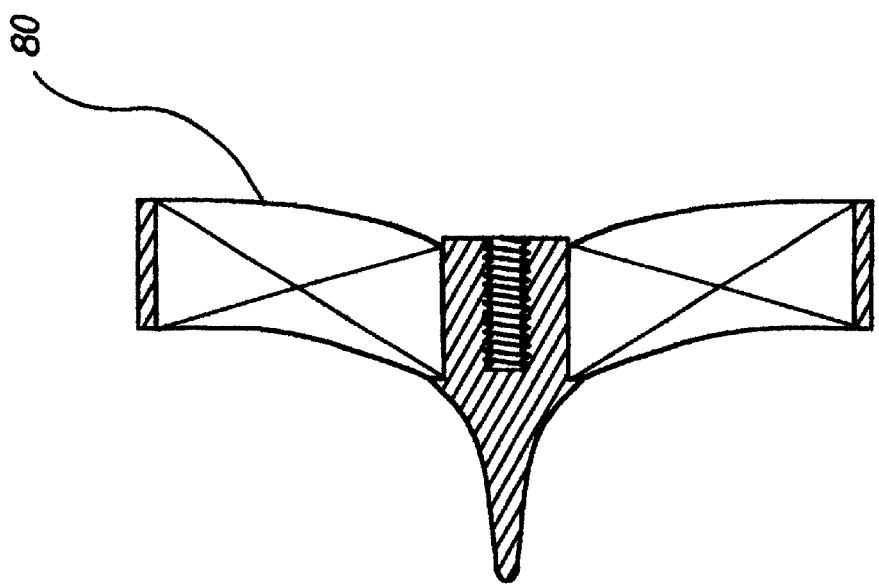
FIG. 6B is a partial view of the cross-section of FIG. 3.
Figure 6A:
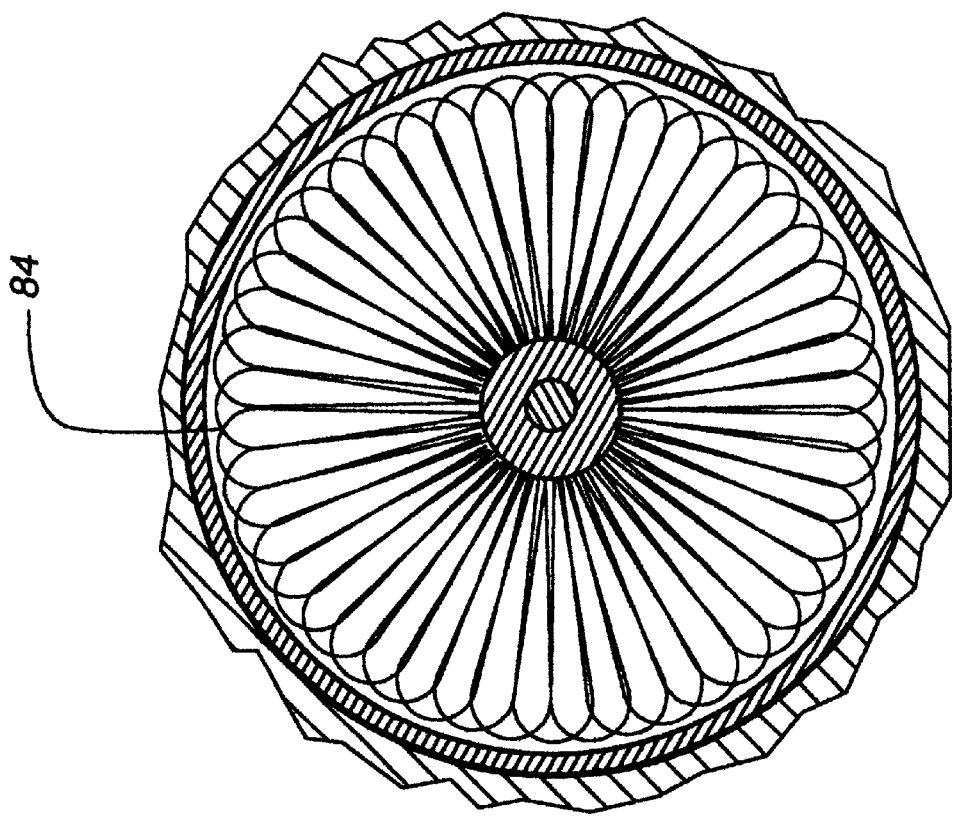
FIG. 6A is a plane view of a cross-section taken through section 6A of FIG. 3.

FIG. 6A depicts section 6A of FIG. 3 in plane view to show the stator 80 and windings 84 of the motor 40 and, similarly, FIG. 6B depicts a partial view of the cross-section of FIG. 3 showing the windings 84 of the stator 80. The motor 40 will be described in greater detail hereinafter.

FIG. 7A depicts section 7A of FIG. 3 in plane view to show the rotor or impeller 21 portion of the motor 40 and to demonstrate the arrangement of the permanent magnets 92 on the rotor. The magnets 92 are arcuately arranged and alternate north pole 91, south pole 93, north pole 91, south pole 93, etc. until the circular arrangement depicted in FIG. 7A is accomplished. FIG. 7B shows section 7A in cross-section to show the rotor 21. The rotor 21 will be described in greater detail hereinafter.

Figure 8:
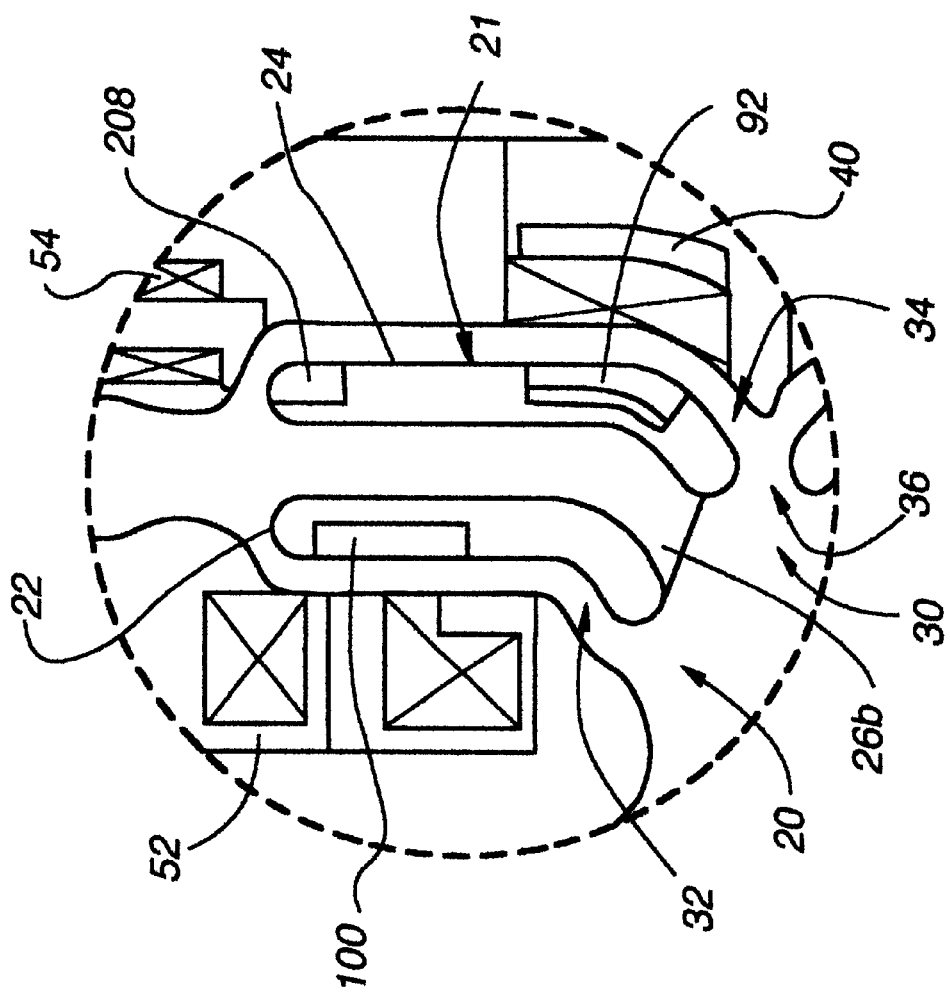
FIG. 8 is an enlarged, fragmentary, cross-sectional view of the pump impeller and housing of FIG. 1.

FIG. 8 is an enlarged, fragmentary cross-sectional view of the pump impeller and housing of FIG. 1. FIG. 8 focuses on a portion of the cross-sections shown in FIG. 3 and can be referred to during the above discussion of FIG. 3 for greater clarity in the details disclosed relative to FIG. 3.

Figure 9:
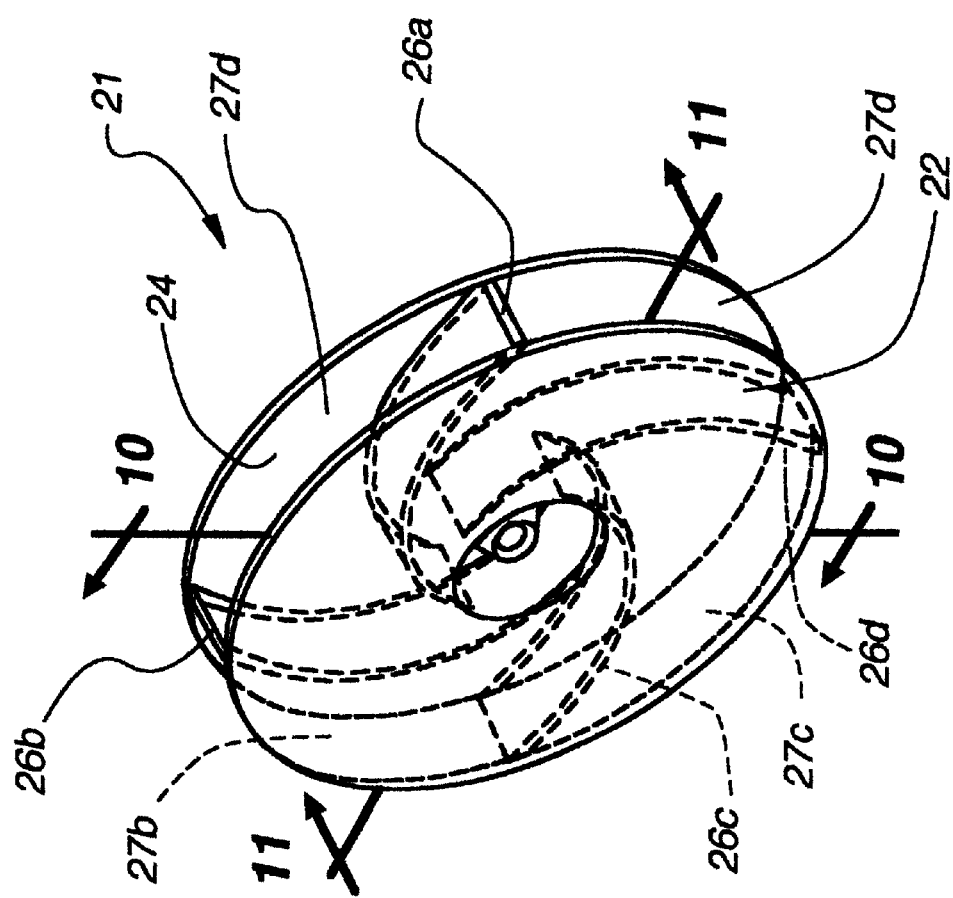
FIG. 9 is a perspective view of the pump impeller of this invention shown in semitransparent mode for clarity.

Pump impeller 21 is configured with two or more impeller vanes, preferably four impeller vanes 26a, 26b, 26c, and 26d, as shown in FIG. 9. Each impeller vane 26a, 26b, 26c, and 26d is mounted between impeller shroud 22 and impeller hub 24 such that impeller chambers 27a, 27b, 27c and 27d are formed between the impeller vanes and the shroud and hub.

Figure 10:
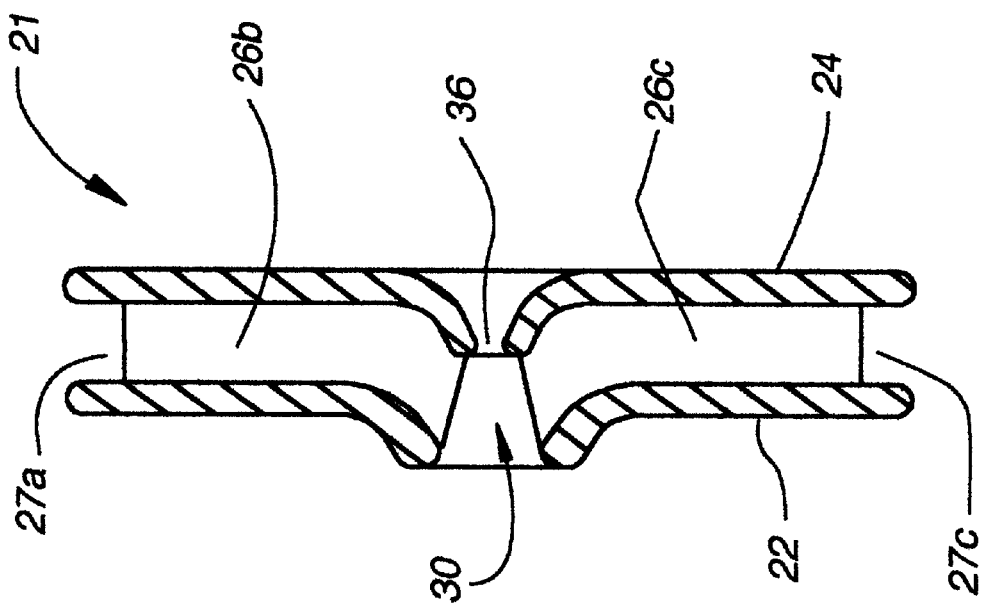
FIG. 10 is a cross-sectional view of the pump impeller taken along line 10—10 of FIG. 9.
Figure 11:
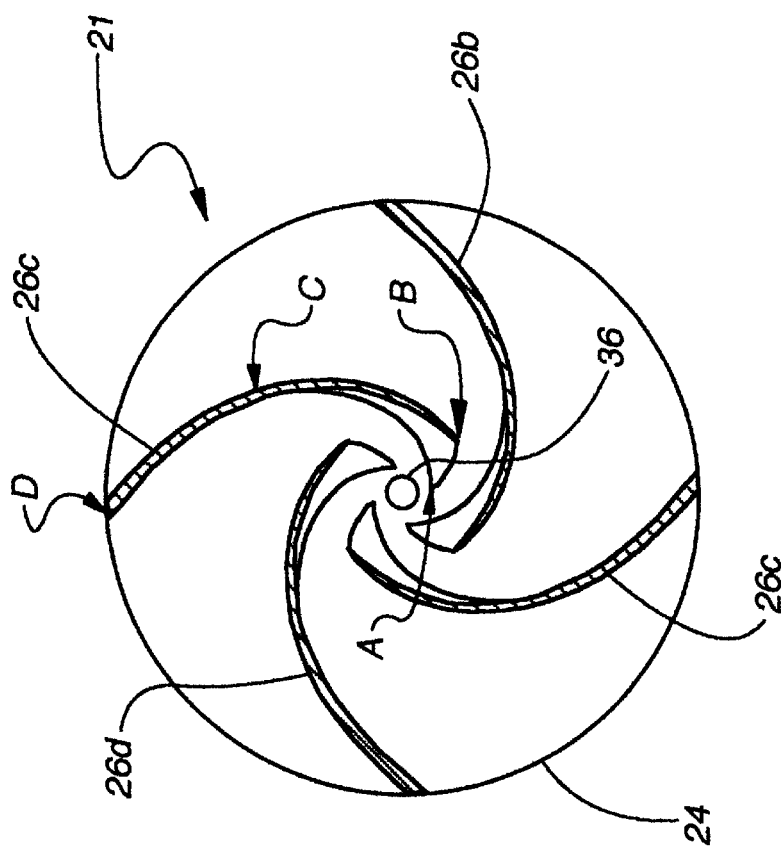
FIG. 11 is a front view of the pump impeller, taken along lines 11—11 of FIG. 9, with shroud assembly removed.

Referring to FIGS. 9, 10, and 11, impeller vanes 26a, 26b, 26c, and 26d are configured with a spiral curvature such that rotation of impeller 21 brings impeller vanes 26a, 26b, 26c, and 26d in contact with fluid to be pumped, thereby causing fluid to move radially toward spiral volute exit 18 (see FIG. 3). Rotation of impeller 21 centrifugally transports fluid from the region at the axial center of construct 10 toward the spiral volute exit 18, correspondingly creating a partial vacuum at the region of impeller intake opening 30 and drawing in additional fluid through intake vessel 19 (FIG. 1). Specifically, as shown in FIG. 11, the impeller is designed to allow for a smooth transition of the flow vector from inlet to outlet. This is accomplished in one particular embodiment employing a blade angle of 17° at the base of the blade at the inlet, A. The blade angle is gradually decreased to 11° at the top of the blade at the inlet, B. Hence the blade is not straight in the axial direction near the inlet. The blade gradually transitions to being straight in the axial direction with an angle of 37° near the midpoint of the blade, C. This 37° angle is maintained to the exit point, D. All blade angles are the inner angles of the blade relative to a tangent to a circle centered in the center of impeller 21. Referring to FIG. 2, the pump volute is located in the pump stationary component to provide a smooth flow of pumped fluid from the discharge of the impeller at relatively high velocity into the pump exit passage where it is slowed down prior to exiting from the pump. The volute increases the fluid pressure (head) by converting fluid kinetic energy (velocity) to potential energy (pressure or head).

The clearance around the impeller 21, in one particular embodiment, is maintained at 0.030" to allow for good washing of the surfaces. Any changes in direction of the flow in the clearance passages are made by maximizing the radius of curvature in order to keep the flow laminar.

Referring again to FIGS. 3 and 8, in one embodiment, a portion of fluid pumped by impeller 21 returns from the region of high pressure near spiral volute 18 along both sides of impeller 21, via first impeller return flow path 32 and second impeller return flow path 34, as reverse flow to region of lower pressure near impeller intake opening 30. Fluid returning along second impeller return flow path 34 also passes through impeller return flow path 36, and thereby serves to equalize internal pressure. The width of impeller return flow paths 32 and 34 are calculated by a precise balance of primary fluid flow and reverse flow, such that fluid does not stagnate within the pump but also does not posses unnecessary inefficiencies.

Pump impeller 21 is suspended within its pump housing by electromagnetic bearing sets 52 and 54 which interact with non-permanently magnetized magnetic targets 100 and 208. A preferred embodiment of the electromagnetic bearing set 52 controls a combination of axial thrust and angular moments with axial position and angular displacements of impeller 21, while electromagnetic bearing set 54 controls a combination of axial thrust and axial position, cooperating with set 52, and radial forces and position on impeller 21. The full electromagnetic suspension of impeller 21 and rotation with an electric motor provides a contact-free operation which increases overall product life and reliability and avoids sensitive fluid damage as discussed herein before. Electromagnetic bearing sets 52 and 54 provide the necessary axial, radial, and moment control forces to counter applied axial and radial forces and applied moments due to fluid, motor forces, impeller gyroscopic effects, gravitational load, acceleration forces, and other incidental forces. Because targets 100 and 208 are formed of non-permanently magnetized magnetic material, no permanent magnets are needed for thrust/moment, or radial/thrust control of the rotor. Thus moment, axial translation, and radial translation of the rotor is controlled by a set of electromagnetic actuators (52 and 54) in the housing positioned to co-operate only with a corresponding set of non-permanently magnetized magnetic material (targets 100 and 208) in the impeller means to keep the impeller centered and under control.

Figure 20:
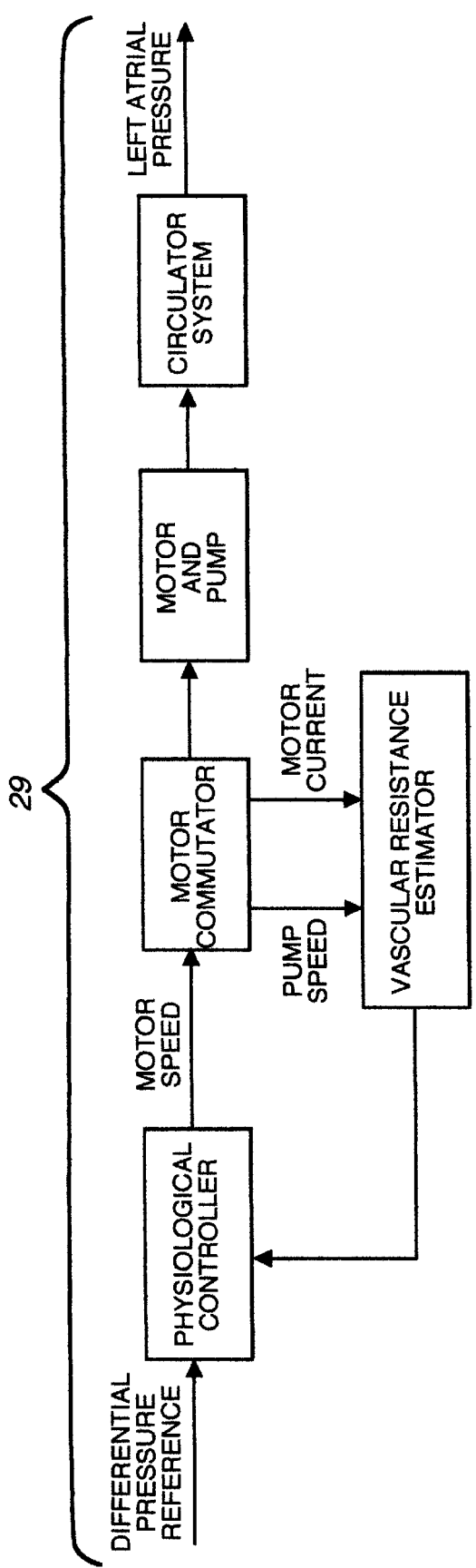
FIG. 20 shows a schematic diagram of a physiological electronic feedback control circuit based on motor current and speed.

As stated above, FIGS. 6A and 6B show a plane view and a cross-section view of a motor stator 80 of the motor 40. Motor 40 is a 3-phase brushless motor and provides electromagnetic force to start and rotate the pump impeller or rotor 21. As shown in FIGS. 7A and 7B, the motor 40 consists of a permanent magnet rotor 21 with permanent magnets 92 imbedded in the hub of a centrifugal or mixed flow pump. The magnets 92 are wedge shaped and arranged to form a circular rotor. The magnets 92 are arranged such that magnetization of the permanent magnets alternate north and south polarities around the rotor 21. Referring to FIGS. 6A and 6B, the motor stator 80 has wire windings 84 excited by current from the electronic controller 29 (FIGS. 1, 20). This stator arrangement produces a magnetic field interacting with the permanent magnets 92 to produce a torque on the rotor 21. It should be noted that permanent magnets 92 form part of the motor 40 and function only to rotate the rotor. They are not involved in thrust/moment or radial/thrust control of the rotor. That function is performed solely by the electromagnetic bearing sets in the stator which interact with the non-permanently magnetized targets in the rotor, as described above.

Although the motor stator 80 can be suspended in at least three configurations depending on torque, speed, and bearing requirements, the configuration of FIGS. 6A and 6B show an ironless configuration for the motor stator. Stator 80 has no saturable magnetic material, thus, minimizing thrust forces created by the motor. As shown in FIG. 6A, wire 84 is wound on a separate fixture and fixed in place on rotor 80 using epoxy or similar material.

The above configuration meets the unique criteria for a centrifugal or mixed flow medical device pump that is needed as was discussed in the background section. The use of permanent magnets in the rotor results in no mechanical contact between the rotor and stator of the motor. The electromagnetic bearing sets 52 and 54 allow the rotor/ impeller 21 to rotate with complete lack of contact with the stator 80. The geometry of the motor meets the requirements of allowing the motor to drive the pump in an efficient manner while providing for laminar flow in the flux gaps with minimal stagnation of blood. This is realized by keeping bending radii large.

Figure 12C:
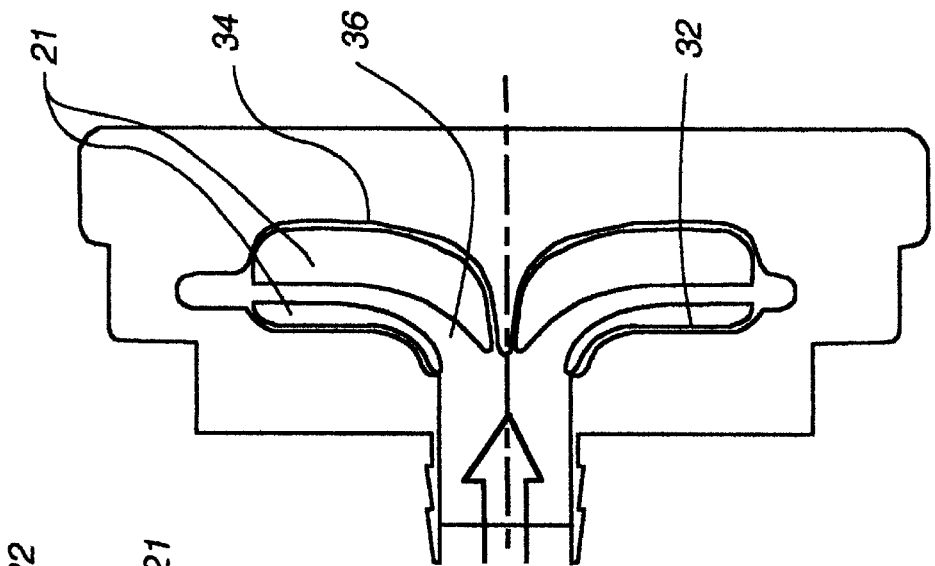
FIG. 12C shows a partial cross-sectional view of the magnetically suspended impeller of the pump described in the present invention.
Figure 12B:
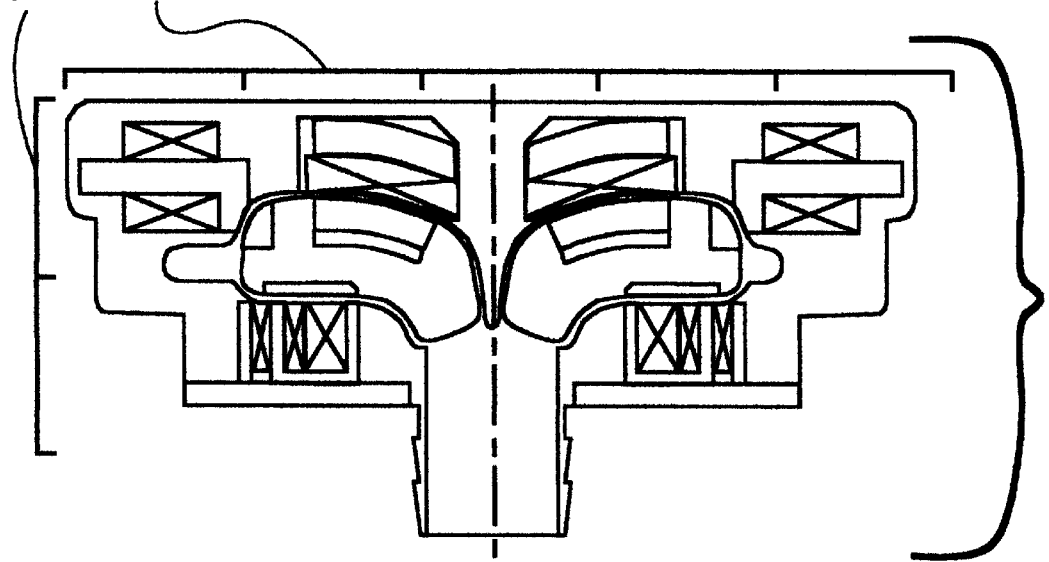
FIG. 12B shows a cross-sectional views of both magnetic components and the magnetically suspended impeller of the pump described in the present invention with an indication of pump cross-sectional dimensions.
Figure 12A:
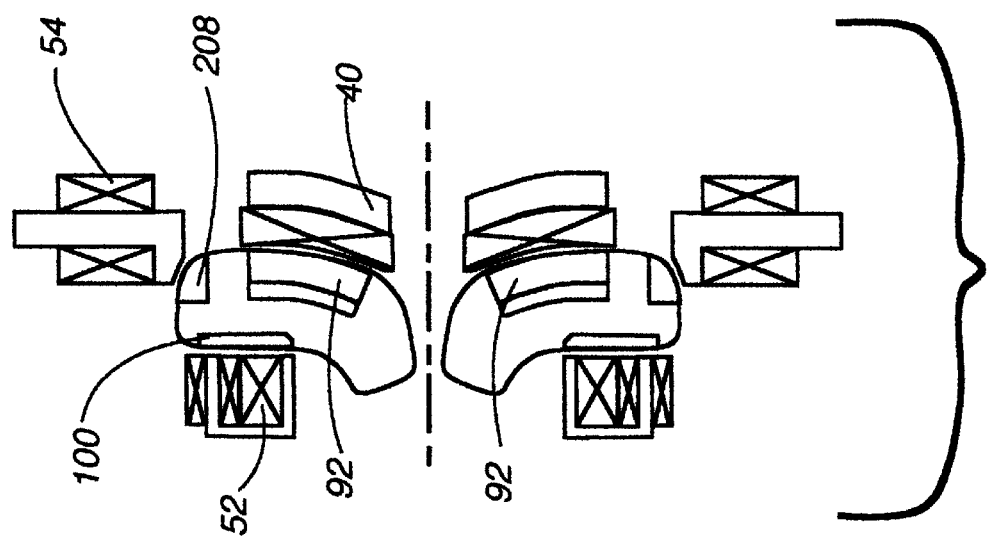
FIG. 12A shows a partial cross-sectional views of magnetic components of the magnetically suspended impeller of the pump described in the present invention.

FIGS. 12A, 12B, and 12C show the layout of one embodiment of the magnetically suspended impeller. Each figure depicts different aspects of the same embodiment. FIG. 12A shows only the magnetic components of the pump. The electromagnets 52, 54 are mounted on the stator (non-rotating component) and the magnetic targets 92 are located on the impeller (rotating component). FIG. 12C shows only the impeller 21 surrounded by the pump housing or stator to emphasize the flow paths 32, 34, and 36. There is no distinct shaft: the impeller is supported and motored directly, thereby reducing length and complexity of the recirculation paths around the impeller and making the device very compact. FIG. 12B depicts a more detailed cross-sectional view of the pump. Graph lines 120 and 121 are shown so as to simplify understanding the scale size of the pump. In one embodiment, graph line 120 is approximately three inches long. Graph line 121 is proportionately scaled to graph line 121. Although other lengths are possible for the graph lines 120 and 121 the invention is typically scaled to fit into the rib cage of a patient that has the pump device implanted into their chest for assistance with heart functioning. When the pump is used in other applications, the scale could be different than the scale of the preferred embodiment.

Figure 13:
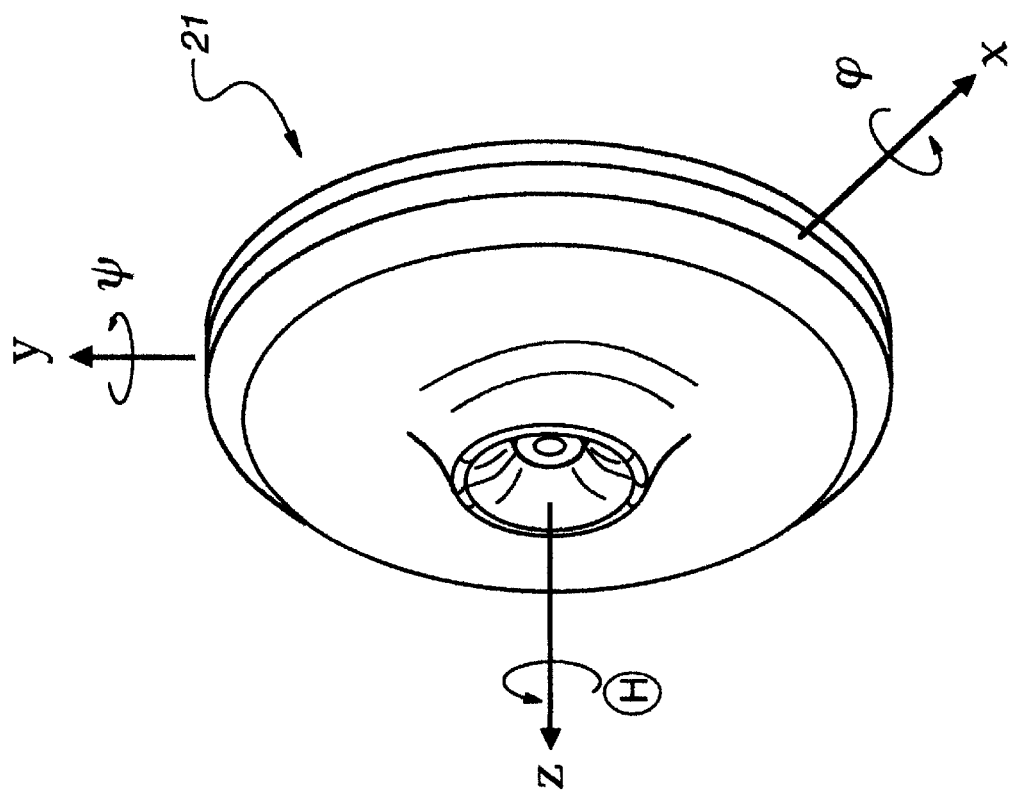
FIG. 13 illustrates the coordinate system and the symbols for the six directions of magnetic actuation for the pump of the present invention.

FIG. 13 shows the coordinate system for defining impeller 21 magnetic actuation in the required six directions: three translations (x,y,z) and three rotations (φ,ψ,θ). All three translational displacements (x,y,z) and two rotations (pitching motions about two axes) (φ,ψ) are held nearly fixed in space relative to the stator by the magnetic forces. The last rotation actuation (θ), about the z axis, is accomplished by the motor.

In a preferred embodiment, the magnetic bearings are constructed in two parts: 1) a thrust/moment configuration and a 2) radial/thrust configuration. As noted above, these forces are controlled by a set of electromagnetic actuators in the housing positioned to co-operate only with a corresponding set of non-permanently magnetized magnetic material (targets 100 and 208) in the impeller means, to keep the impeller centered and under control. No permanent magnets are required for thrust/moment, or radial/thrust control of the rotor. First, as shown in FIG. 14, the thrust/moment bearing configuration is a circular array of eight horseshoe electromagnets 52, which are directed at target 100 on the inlet face of the impeller. Although numerous arrangements could be used to form a four quadrant actuator, in this embodiment, eight coils are used with the activation coils and are wound in pairs so that there are four quadrants of control. This provides a combination of axial actuation (z) and pitching moments (φ,ψ). The thrust force (z) is generated by imposing equal coil currents on all of the coils so that each magnetic pole in the electromagnetic bearing exerts the same force on the target. The pitching angular actuation forces (moments) are produced by applying different coil currents to coils on opposing coils above and below the impeller centerline (φ angular displacement) and to the left and right of the impeller (ψ angular displacement). The function of the electronic controller is to determine what combination of currents must be employed to control these axes.

Second, similar to FIGS. 4A and 5A, FIG. 15A shows a plane view of the radial/thrust and thrust/moment bearing configurations. The radial/thrust bearings comprise four horseshoes (including eight pole faces, 301–308). The eight pole faces of the thrust/moment bearings are shown at 309–316. FIG. 15B shows a side view of the impeller 21 depicting a target 208 which is the radial/thrust bearing target with a tapered magnetic face (also shown in detail at 208 in FIGS. 3 and 7B). FIG. 15B also shows another target 100 which is the thrust/moment bearing target (see also FIG. 3). Bearing targets 208 and 100 are preferably formed of non-permanently magnetized magnetic material, such as soft iron or iron-cobalt alloys. Accordingly, with this bearing configuration, there is at least one axis which is controlled ONLY by magnetic materials in the rotor that are not permanently magnetized, interacting with electromagnetic bearing sets in the stator. Thus the control of at least one axis does not need the use of permanent magnets in the rotor.

The prior art discloses permanent magnet sets in the rotor of an electromagnetically suspended pump, but for each permanent magnet set in the rotor, requires BOTH a permanent magnet set in the stator AND an electromagnetic set in the stator, for thrust/moment, or radial/thrust control of the rotor. However, the prior art does not clearly teach that any axis may be controlled solely by the interaction of stator electromagnetic actuators interacting only with non-permanently magnetized magnetic material in the rotor. This novel control configuration introduces significant complications in the control of the rotor, but also provides significant benefits. If a permanent magnet set is disposed in the rotor, the force can be controlled bidirectionally, i.e., it can be made both attractive or repulsive, because of the polar nature of permanently magnetized magnetic material. However, with the use of only non-permanently magnetized magnetic material in the rotor, the force is always attractive. This necessitates a completely different and novel control algorithm for maintaining impeller position. However, removal of permanently magnetized magnetic material from the rotor advantageously reduces the size, weight, and complexity of the device. This reduction in size, weight, and complexity represents a significant advance in the art, and is made possible by this unique rotor positional control configuration.

This magnetic bearing configuration can exert control forces in the axial direction (z), 1 radial directions (x,y), and angular displacements (φ,ψ). These two magnetic bearing configurations, the thrust/moment and the radial/thrust configurations, provide eight independent electromagnetic coil currents which produce the necessary electromagnetic forces and moments required to keep the impeller centered and under control without the use of permanent magnets in the rotor.

The operation of the electromagnet horseshoes in this embodiment is simplified and enhanced by employing a bias current. This bias current is employed in all of the coils but may differ from bearing configuration to bearing configuration. The bias current allows the bearings to operate with control coil currents in a linear fashion about the steady state bias current. Also, the bias current provides a substantial dynamic force generation capability of the magnetic bearing configuration. In this application, large bias currents will produce high heat generation, which is not desirable for use in human sensitive fluids such as blood. Thus, low bias currents are employed to reduce the heat generation.

An electronic controller 29 (FIGS. 1, 20) is provided in the invention to automatically adjust the activating bearing coil currents in electromagnetic bearing sets 52 and 54 which, in turn, adjust the control forces and moments exerted by the magnetic bearings on the rotating impeller 21 in response to the applied forces and moments. Such electronic controller is continuously provided with an electronic signal which is related to the position or velocity or acceleration, or a combination of position, velocity and acceleration, of the rotating impeller in the available clearance space inside the pump frame during operation. The invention also provides switching or direct current power amplifiers and power supplies necessary to operate the electromagnetic actuators in the magnetic bearings.

Figure 16A:
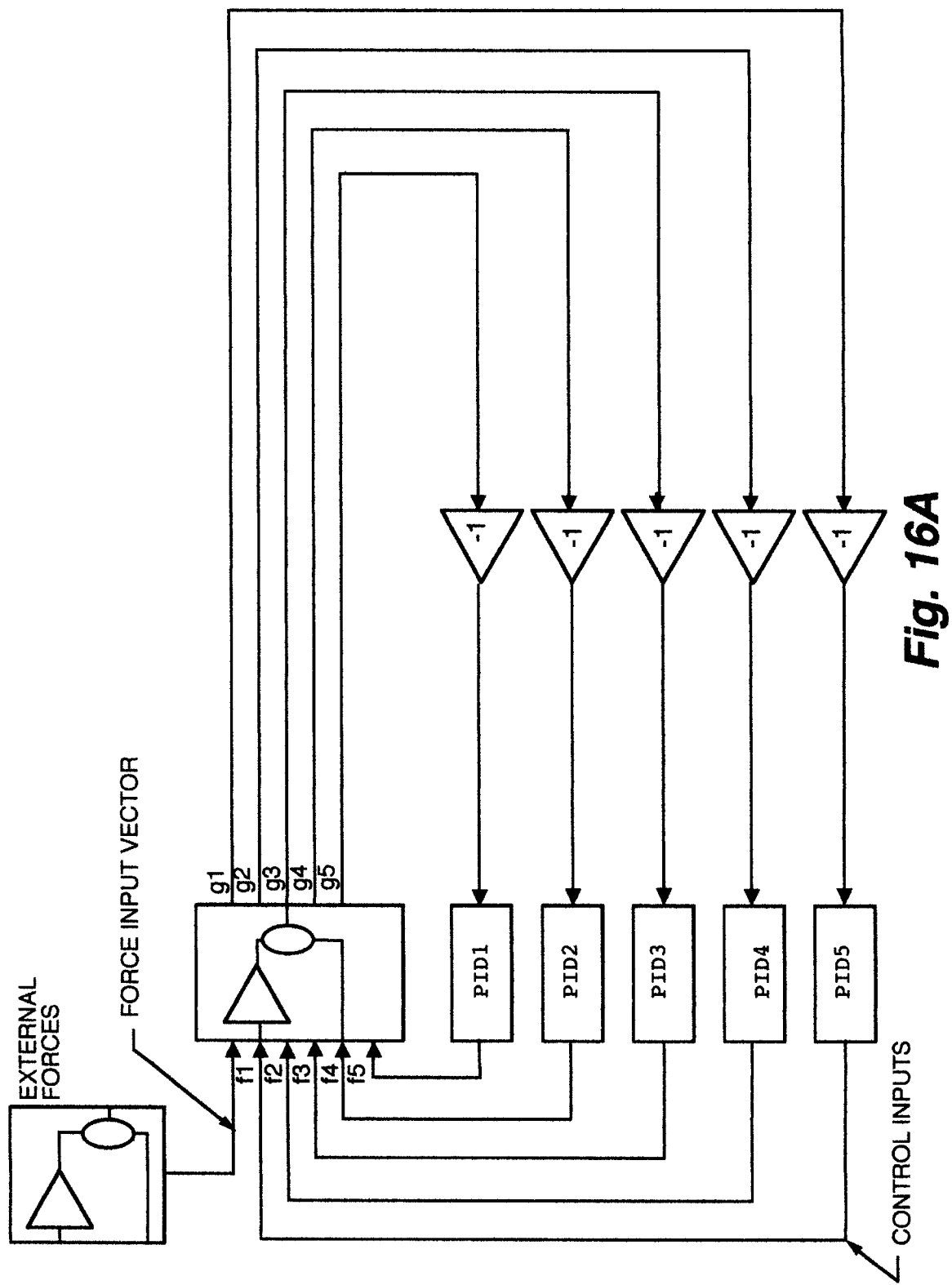
FIG. 16A shows electronic circuits that provide electronic feedback for control of the impeller position within the stator clearance region.
Figure 16B:
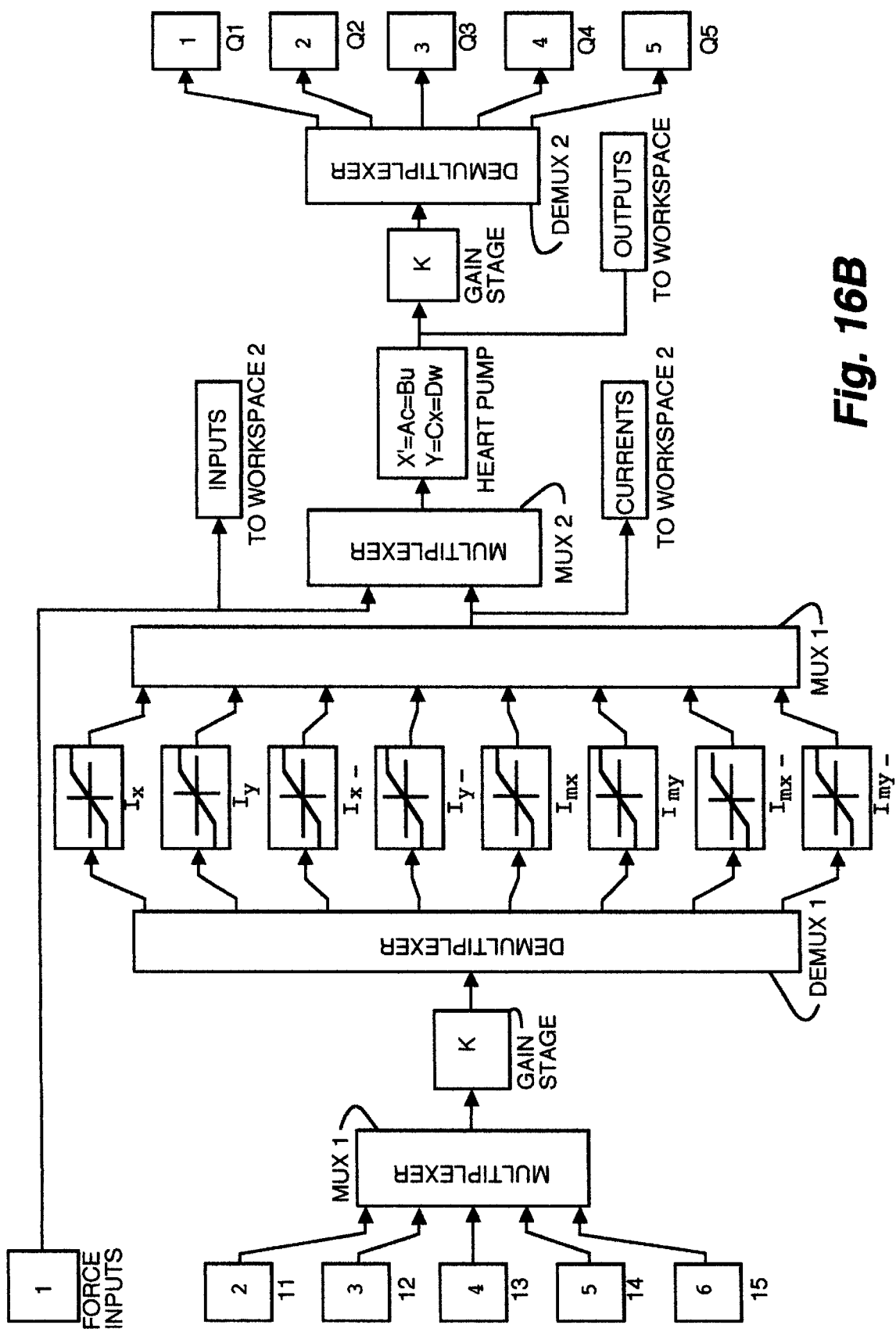
FIG. 16B shows further details of the electronic circuits of FIG. 16B that provide electronic feedback for control of the impeller position within the stator clearance region.

FIGS. 16A and 16B show an embodiment of the electronic circuits for electronic feedback control of the impeller position within the stator clearance region. Electronic circuits composed of resistors, capacitors, amplifiers, etc. are combined to control the impeller dynamics using proportional-integral-derivative control methods or other linear control algorithms such as state space, mu synthesis, linear parameter varying control, and nonlinear control algorithms such as sliding mode control. Particular control algorithms are used to take into account impeller rigid body gyroscopic forces, fluid stiffness, damping and inertia properties whose magnitude depend upon impeller position, rotational rate, pressure rise, and flow rate. In one embodiment, the physical circuits are miniaturized using surface mount technology, very large scale integrated (VLSI) circuit design and other means.

In the embodiment shown here, the control algorithm produces the eight coil currents which control the three displacements (x,y,z) and two angular displacements ($\phi,\psi$). The controller algorithm design is robust to account for uncertainties in forces acting on the impeller such as fluid stiffness, damping and inertia properties, gyroscopic effects, magnetic forces, etc. The control algorithms are implemented on a dedicated microprocessor with adjustable parametric variation implementation to account for different physiological needs for the different applications to different size humans, from children to large adults.

Power amplifiers are employed in the invention to produce the desired coil currents for the electromagnetic bearings as determined by the electronic controller output voltage. One embodiment of a switching amplifier, operating with voltage switched either on or off at a frequency much higher than the rotational frequency of the pump impeller, is utilized in the device because power amplifiers are very efficient, having an efficiency in the range of 85 to 99%. The electronic power circuits are composed of magnetic coils, with associated resistance and inductance, resistors, capacitors, semiconductor components. The coils are implemented using wire with low resistance.

These power circuits are designed to be regenerative— that is, the magnetic bearing enabling power moves back and forth between the magnetic coil inductors to the capacitors with the only losses occurring due to the low coil resistance (ohmic losses). The high power present in the magnetic coil circuits is a small fraction of the nominal power capability; the nominal power capability being defined as supply voltage times average switched current in the coils. With these low power switching amplifiers and regenerative coil power circuits, the undesirable heating of the blood is kept to a minimum.

The invention is designed to generate the electronic signal related to the position, velocity or acceleration of the rotating impeller through one of the following: (i) a physical device such as an eddy current, induction, optical, capacitance or other approach; or (ii) a combination of the current and voltage waveform provided to the activating coils in the magnetic bearings. In the case of a physical sensor device placed in the pump frame near the clearance gap between the frame and the rotating impeller, the electronic position, velocity, or acceleration signal, is obtained from signal conditioning electronics and wiring provided for input of the signal into the electronic controller for the magnetic bearings.

In the case of a self-sensing signal, the signal conditioning is provided for determining the position, velocity, or acceleration of the rotating impeller without a physical device, which is allows for a minimum number of wires required in the wiring pathways between the electromagnetic actuators and the electronic controllers.

Figure 18:
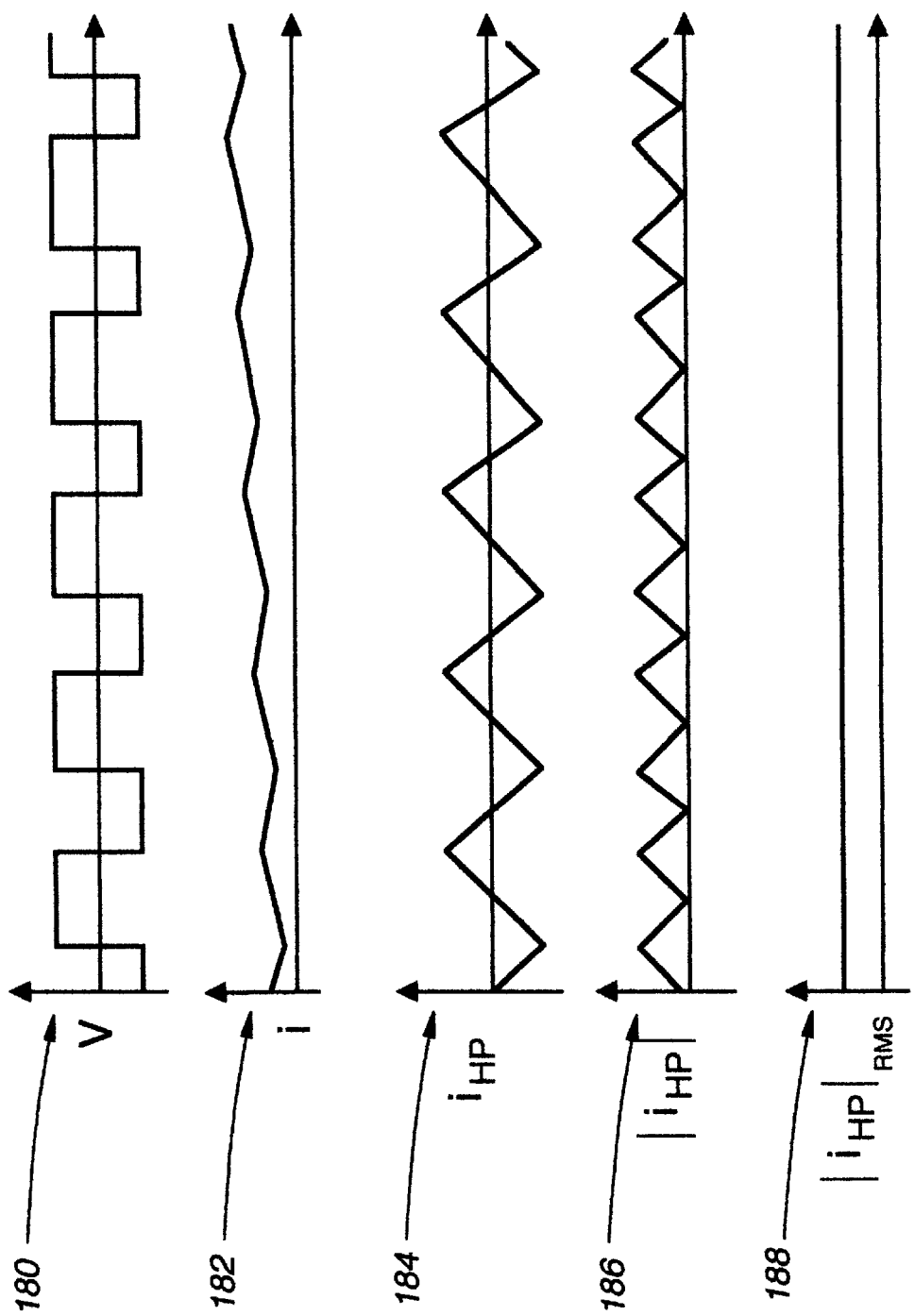
FIG. 18 illustrates a table of graphs of the signals as they pass through the filters of FIG. 17.

A preferred embodiment of the sensing function of the invention is the self sensing configuration. The self sensing configuration avoids the use of a physical sensor in the stator, minimizes the size of the pump, and minimizes the number of wires required for operation. In one embodiment illustrated in FIGS. 16A and 16B, position sensing is accomplished by examining the voltage and current switching wave forms (employed with the switching power amplifiers described above) for several of the electromagnetic coils. Each coil is driven by a switching power amplifier with a high (in the kHz range) carrier frequency. The resulting current waveform, one version which is shown in FIG. 18, is a combination of the relatively low frequency commanded waveform (to produce the necessary control force for positioning the impeller) and a high frequency triangular waveform due to the high frequency carrier. The amplitude (magnitude) of this commanded waveform is a function of the circuit inductance (a combined inductance due to the magnetic material properties in the magnetic bearing and due to the fluid gap), the switching frequency, the power supply voltage, and the duty cycle of the switching amplifier (ratio of on to off voltage employed in amplifier to produce the desired control forces).

Figure 17:
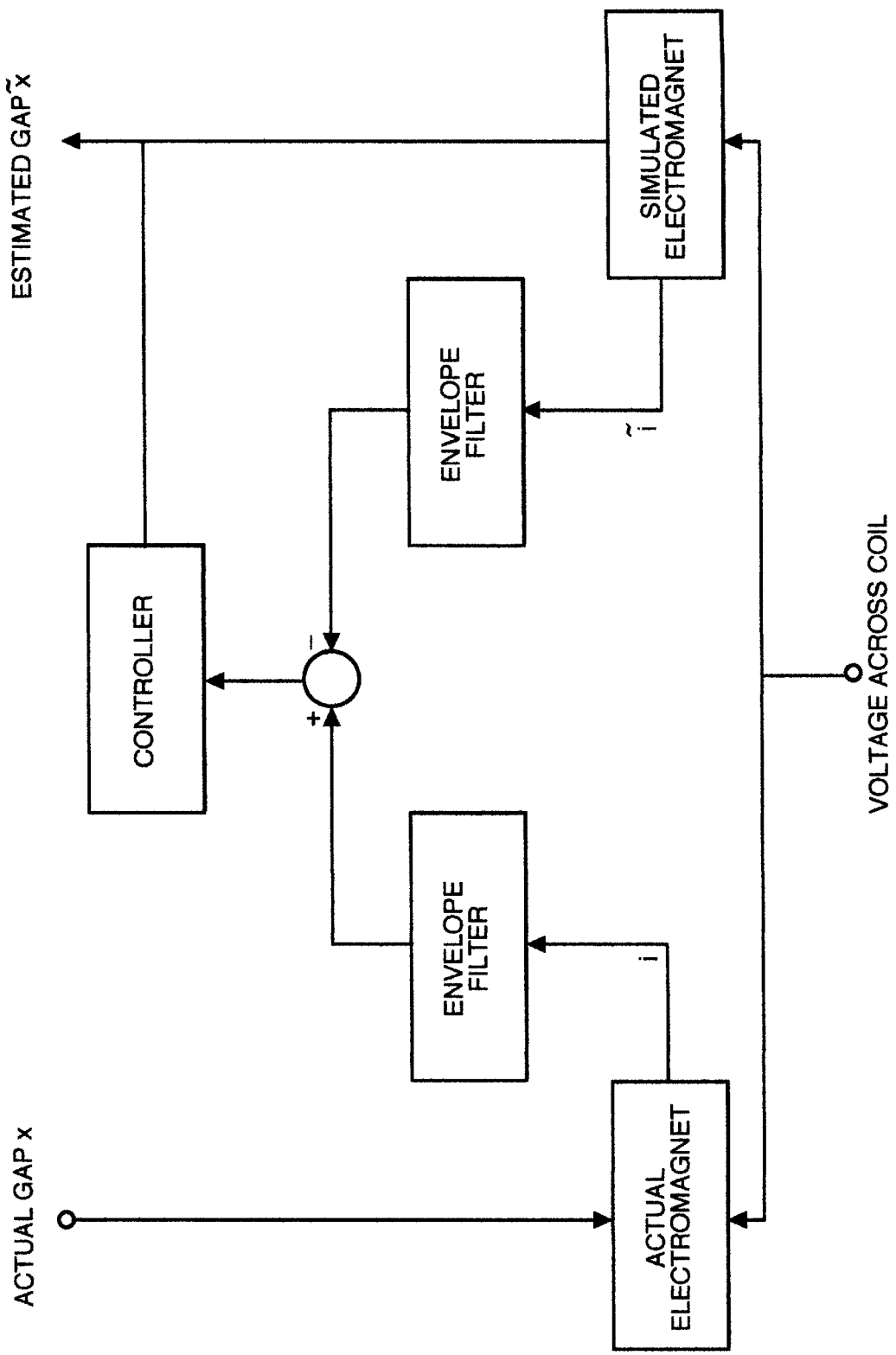
FIG. 17 illustrates electronic filters from a self sensing part of the invention, the filters extracting fluid gap dimension information while removing the effects of power supply voltage, switching frequency, duty cycle variation, and electronic or magnetic noise.

FIG. 17 shows an embodiment of electronic filters that are provided in the self sensing part of the invention to extract the fluid gap dimension information while removing the effects of power supply voltage, switching frequency, duty cycle variation, and electronic or magnetic noise. A parameter estimation method is employed to demodulate the signal and determine the fluid gap dimension. One embodiment of the envelope of filters is employed, consisting of a high pass filter to remove the bias current, a precision rectifier to make the waveform strictly positive, and a low pass filter to remove the variation in the remaining signal. The embodiments shown in FIG. 17 gives a low noise sensor with a high bandwidth, suitable for the self sensing signal determination of the fluid gap dimension.

FIG. 18 shows the sequence of signal forms as they pass through the filters: the graph at 180 shows the supply coil voltage, the graph at 182 shows a typical actual coil current waveform, the graph at 184 shows the current signal output from the integrator (described in detail in FIG. 19) which removes the change in coil current due to the control of the externally imposed forces and moments, the graph at 186 shows the rectified version of 184, and the graph at 188 shows the time average of 186 extracted using a low pass electronic filter.

Figure 19:
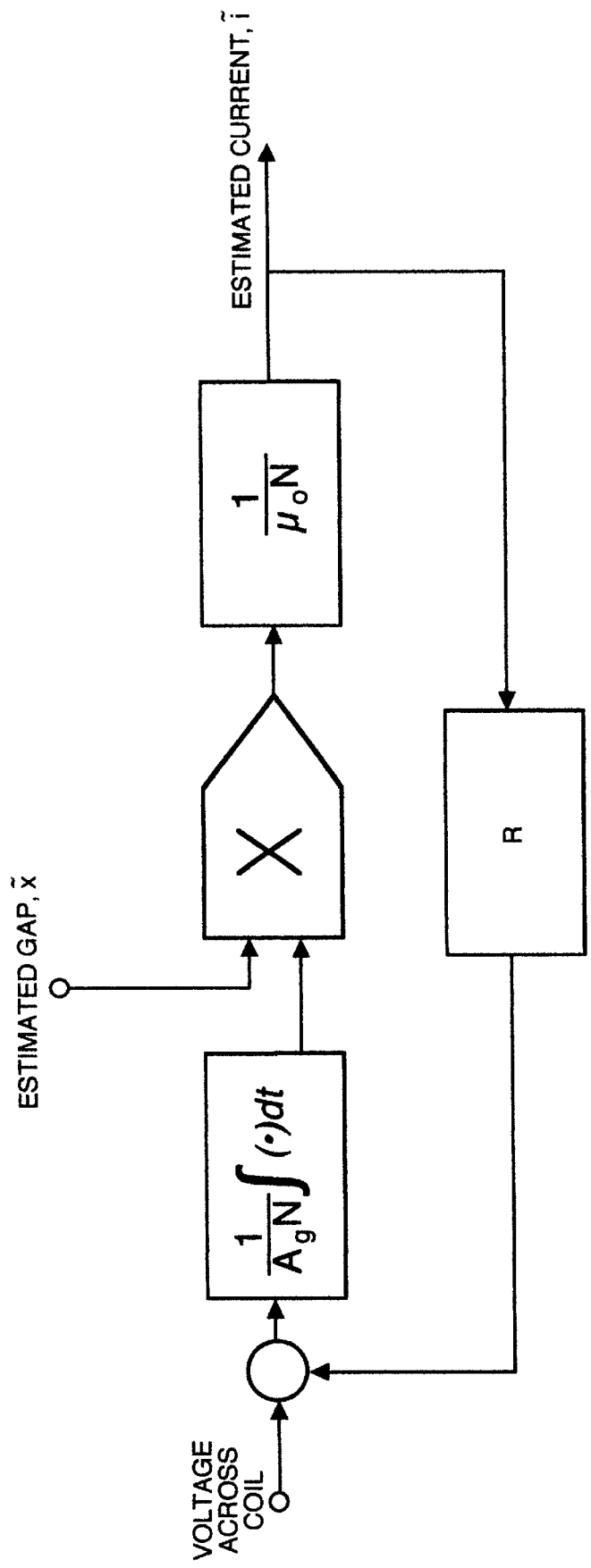
FIG. 19 depicts a schematic diagram of an integrator circuit whose gain is controlled by an analog multiplier indexed to the estimated gap.

FIG. 19 shows a circuit which extracts the change in coil current due to the control of the externally imposed forces and moments. This is shown in the preferred embodiment of a negative feedback circuit, which comprises an integrator whose gain is controlled by an analog multiplier indexed to the estimated gap. This feedback circuit includes a proportional-integral device where the estimated displacement and the integral of the estimated displacement are combined to form the negative feedback signal and then compared to the original voltage waveform to provide the desired current waveform proportional to the impeller displacement.

The use of pumps for sensitive applications often requires adjustment of flow rates and pressure rises such as in the artificial heart where the physiological conditions change significantly. For example, the body may be resting or sleeping with a rather low required flow rate and pressure rise whereas if the body is undergoing exercises, such as walking, a much higher flow rate and pressure rise is required. In the invention, the primary method of adjusting the flow rate and pressure rise is by varying the motor speed. In physiological applications, the pump inlet pressure is called the preload while the pump exit pressure is called the afterload.

A second embodiment of the physiological controller uses an indirect measurement of pressure rise from the inlet of the pump to the outlet of the pump (i.e., Pout-Pin). At a given flow rate, changes in pressure across the pump are an indication of changes in systemic resistance in the circulation system of the patient. Change in systemic resistance is known to be one indicator of increased physical exertion in humans. Thus, a measurement of pressure difference from outlet to inlet is used as a basis for a physiological controller.

The measurement of pressure difference from inlet to outlet can be indirectly measured by two methods which are (1) measurement of motor current and pump speed, or (2) measurement of bearing current, or some combination thereof.

The first method to measure pressure indirectly uses measurements of motor current and pump speed. These measurements are used in an electronic controller to derive pressure based on equations and/or tables electronically stored in the controller. The relationship between current, speed, and pressure rise is characterized and calibrated prior to operation, providing the basis for the controller. The block diagram for the implementation of the controller 29 is shown in FIG. 20.

Figure 21:
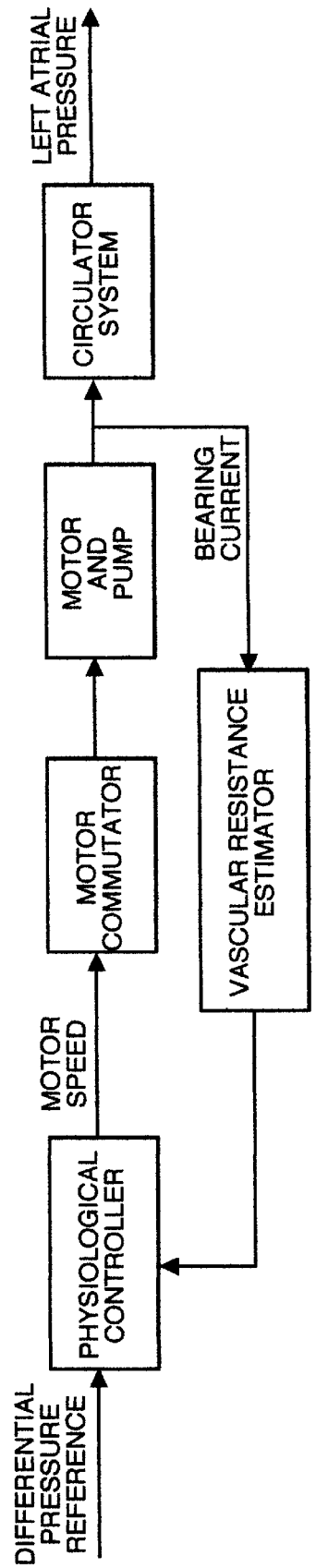
FIG. 21 shows a schematic diagram of a physiological electronic feedback control circuit based on bearing current.

The second method to measure pressure rise indirectly uses magnetic bearing current. It is well known that current in an active magnetic bearing is directly related to force on the rotor. The pressure difference from outlet to inlet of the pump can be derived directly from the resultant net force on the impeller due to the pressure difference. Hence, the bearing current can be used in an electronic controller to derive the pressure difference from outlet to inlet of the pump. The block diagram of the implementation of the controller is shown in FIG. 21.

Figure 22:
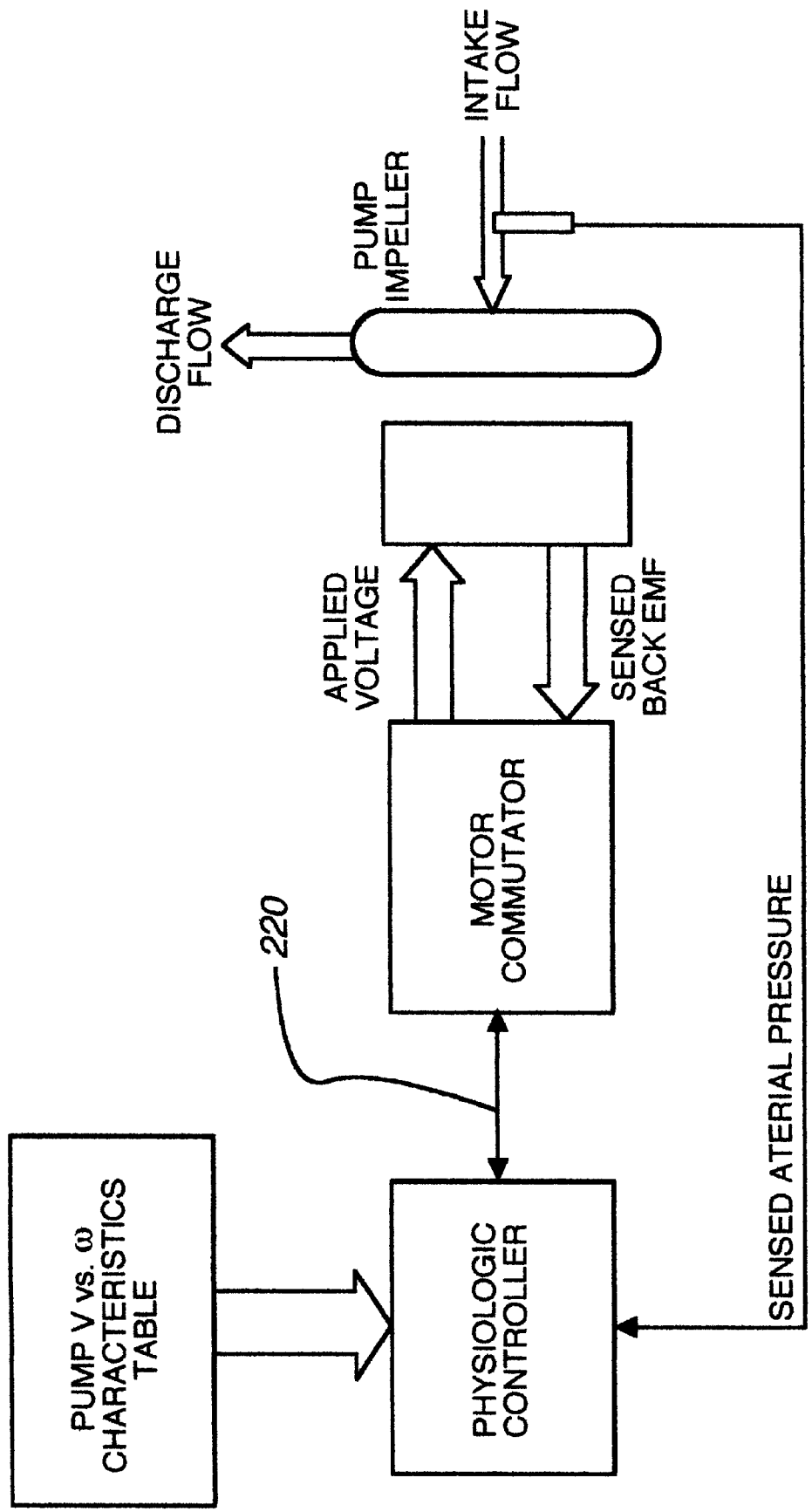
FIG. 22 shows a physiological electronic feedback control circuit for regulating the motor speed relative to preload and afterload signals.

FIG. 22 shows another embodiment of a physiological electronic feedback control circuit that is provided in the invention to regulate the motor speed relative to the preload and afterload signals thereby properly controlling the motor speed. The physiological control circuit is provided to regulate the pump flow rate and pressure rise to meet the physiological needs of the biological application. Reference number 220 indicates an interface between the physiological controller and the motor commutator such that a desired speed signal is sent to the motor commutator and an actual speed signal is sent to the physiological controller. Thus, the embodiment of FIG. 22 illustrates motor control based on physiological parameters.

In addition to electronic signals relating to the preload and afterload forces internal to the pump, the electronic signals from the activating coil currents in the electromagnetic bearings are related to other forces such as the gravitational loading and acceleration effects relating to the beginning of motion and the stopping of motion. Also, electronic signals related to the acceleration are obtained by sensing, either in the pump housing or other location of known position relative to the pump, the acceleration in one, two, or three orthogonal directions. The electronic acceleration signals are then employed in the invention to subtract that signal from the preload and afterload signals, as described above. The resulting difference signal is then used for the physiological controller described above.

The speed of the motor is related to the physiological performance of the pump. The motor feedback emf is used to sense the rotational speed of the motor rotating about the pump impeller axis and to develop an electronic signal proportional to the impeller rotational speed. The impeller rotational speed signal is provided to the electronic physiological feedback controller described above. The present motor rotational speed is used in combination with the preload and afterload signals to adjust future motor speeds to match physiological pump flow rate and pressure rise needs based upon body requirements.

The Method

Elements of construct 10 are operable in singular mode as a ventricular assist device, or paired for a total artificial heart. In the case of the total artificial heart which utilizes two of construct 10, each construct 10 operates entirely independent of the other construct, thereby eliminating complex control equipment and circuits that would otherwise be required if both constructs were combined.

The physiologic controller (not shown) senses fluid pressure inside intake vessel 19 and generates an electrical signal to modify rotational speed of motor 40 according to specific algorithms determined by electronic controller (not shown). The physiologic controller may signal a change in rotational speed of motor 40 to compensate for a change in fluid pressure inside intake vessel 19 yet avoid excessive rotational motor speed that would collapse vessels. In addition to controlling rotational speed of motor 40, the physiologic controller (not shown) senses position, velocity, and/or acceleration information of impeller 21 via eddy current, induction, optical, capacitance or other self-sensing electronic signals and generates an electrical signal that is sent to the electronic controller (not shown), which correspondingly provides adjustment to electrical current in electromagnetic bearing sets 52 and 54 thereby providing adjustment to control forces. Adjustments to electromagnetic bearing sets 52 and 54 compensates for applied forces due to fluid, motor forces, gravitational load, acceleration forces, and other incidental forces.

The rotation of impeller 21 brings impeller vanes 26a, 26b, 26c, and 26d in contact with fluid to be pumped, thereby causing fluid to move radially toward spiral volute exit 18. The centrifugal transport of fluid from the region at the axial center of construct 10 toward the spiral volute exit 18 correspondingly creates a partial vacuum at the region of impeller intake opening 30 and draws in additional fluid through intake vessel 19. The unique log spiral configuration of spiral volute exit 18 then transports sensitive fluid along the region near the circumference of construct 10 in a smooth, non-turbulent and low thermal manner to outlet vessel 15. Outlet vessel 15 is connected to anatomical vessels or other mechanisms.

A portion of fluid pumped by impeller 21 returns from the region of high pressure near spiral volute 18 along both sides of impeller 21, via first impeller return chamber 32 and second impeller return chamber 34, in the form of reverse fluid flow to the region of lower pressure near impeller intake opening 30. Fluid returning along second impeller return chamber 34 also passes through impeller return opening 36, and thereby serves to equalize internal fluid pressures and prevent flow in the clearance passages from sensitive fluid stagnation.

If construct 10 is to be operated in pulsatile mode, rotational speed of impeller 21 is varied and controlled by the electronic controller (not shown), which adjust electrical current in motor 40, thereby accelerating and decelerating the rotation of impeller 21 and causing fluid to be pumped in a pulsatile fashion.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. Apparatus for pumping sensitive biological fluids comprising:
    a construct having an exterior, a hollow interior having walls therein, and an axial center;
    an inlet formed from the construct exterior for passage of fluids therethrough and into the hollow interior of the construct;
    an outlet formed from the construct exterior for passage of fluids therethrough from the hollow interior of the construct, the outlet radially located from the axial center of the construct;
    an impeller means disposed within the hollow interior of the construct and out of contact therewith for controlling fluid flow into the inlet, through the hollow interior of the construct, and out of the outlet, the impeller means having arcuate blades and arcuate passageways whereby fluid flow through the construct is gradually redirected from the inlet to the outlet;
    a magnetic means for suspending the impeller means out of contact with the hollow interior of the construct, said magnetic means providing control over five degrees of freedom of motion of the impeller means, including (i) one axial translational axis, (ii) two radial translational axes, and (iii) two rotational axes controlled for moment, wherein at least one of the five axes controlled for moment, axial translation, and radial translation is controlled by a set of electromagnetic actuators in the construct positioned to cooperate only with a corresponding set of non-permanently magnetized magnetic material in the impeller means; and
    a motor means for selectively rotating the impeller means to thereby control fluid flowing through the apparatus.

2. Apparatus of claim 1 wherein the construct comprises a first pump housing half and a second pump housing half hermetically sealed to the first pump housing half for forming the hollow interior of the construct.

3. Apparatus of claim 2 wherein the first pump housing half comprises a pump inlet vessel having an inlet throughbore, the pump inlet vessel forming the inlet within the construct exterior for passage of fluids therethrough and into the hollow interior of the construct.

4. Apparatus of claim 2 wherein the first and the second pump housing halves each include a protrusion wherein a pump outlet vessel having an outlet throughbore is formed from hermetically sealing said protrusions, the pump outlet vessel forming the outlet within the construct exterior for passage of fluids therethrough from the hollow interior of the construct.

5. Apparatus of claim 1 wherein the impeller means comprises an integrated combination of an impeller for fluid flow through the construct and a rotor being controlled by the motor means thereby allowing the motor means to control rotation of the impeller means, the integrated combination of the impeller and the rotor forming interior sides of a first return flow chamber and a second return flow chamber respectively for permitting fluid flow around the suspended impeller means.

6. Apparatus of claim 5 wherein the interior side of the impeller forming the first return flow chamber includes a first member having a curvature corresponding to a curvature of walls of the hollow interior of the construct.

7. Apparatus of claim 6 wherein the impeller includes a first electromagnetic magnetic material for interaction with a first electromagnetic bearing set, wherein the first electromagnetic bearing set stabilizes the impeller means and controls an axial position and external thrust forces and moment which act upon the impeller means.

8. Apparatus of claim 6 wherein the impeller includes a first electromagnetic magnetic material for interaction with a first electromagnetic bearing set, wherein the first electromagnetic bearing set stabilizes the impeller means and controls a combination of an axial position, two degrees of freedom angular displacements, external thrust forces, and external moments which act upon the impeller means.

9. Apparatus of claim 5 wherein the interior side of the impeller forming the second return flow chamber includes a second member having a curvature corresponding to a curvature of walls of the hollow interior of the construct, the second member being coupled to a first member by the arcuate blades of the impeller means wherein impeller chambers are formed from (i) the arcuate blades, (ii) the first member, and (iii) the second member, thus forming the arcuate passageways for the gradual redirection of fluid from the inlet to the outlet.

10. Apparatus of claim 9 wherein the second member includes a second magnetic material for interaction with a second electromagnetic bearing set, wherein the second electromagnetic bearing set controls two degrees of freedom in radial position and external radial forces which act upon the impeller means.

11. Apparatus of claim 9 wherein the second member includes a second magnetic material for interaction with a second electromagnetic bearing set, wherein the second electromagnetic bearing set controls a combination of two degrees of freedom in radial position, axial position, external radial forces, and external thrust forces which act upon the impeller means.

12. Apparatus of claim 10 wherein the second magnetic material comprises a position on the second member such that the second electromagnetic bearing set controls a combination of two degrees of freedom in radial position, axial position, two degrees of freedom in angular position, external radial forces, thrust forces, and external moments which act on the impeller means.

13. Apparatus of claim 9 wherein the second member comprises a rotor integrally formed therein and the rotor having a plurality of permanent magnets disposed thereon for interaction with the motor means wherein the rotor may be rotated by the motor means and thereby rotate the impeller means.

14. Apparatus of claim 1 wherein the magnetic means comprises an arrangement of a first electromagnetic bearing set disposed on a wall of the hollow interior of the construct, a second electromagnetic bearing set disposed on another wall of the hollow interior of the construct, a first piece of non-permanently magnetized magnetic material disposed on the impeller means and corresponding to the first electromagnetic bearing set, and a second piece of E[] non-permanently magnetized magnetic material disposed on the impeller means and corresponding to the second electromagnetic bearing set, wherein the impeller means is prevented from contacting the hollow interior of the construct by magnetic fields between (i) the first electromagnetic bearing set and the first piece of non-permanently magnetized magnetic material and between (ii) the second electromagnetic bearing set and the second piece of non-permanently magnetized magnetic material.

15. Apparatus of claim 14 wherein the magnetic means includes an electronic controller for controlling electric current in the first and the second electromagnetic bearing sets.

16. Apparatus of claim 15 wherein the electronic controller comprises a physiological controller for controlling a rate of rotation of the impeller so that the rate of rotation corresponds to the physiological state of a person using the apparatus of the present invention.

17. Apparatus of claim 14 wherein the arrangement comprises the first electromagnetic bearing set being positioned at an angle from the first magnetic material such that the electromagnetic bearing set is used to control two degrees of freedom of the impeller means.

18. Apparatus of claim 14 wherein the arrangement comprises self sensing means for dynamically positioning the impeller means during operation such that the impeller means is constantly out of contact with the construct.

19. Apparatus of claim 14 wherein the arrangement comprises electromagnetic bearing sets having a force strong enough to overcome acceleration forces.

20. Apparatus of claim 1 wherein the motor means comprises a stator integrally formed within a wall of the hollow interior of the construct, the stator having windings fixed therein for receiving current from a motor controller.

21. Apparatus of claim 1 wherein the motor means comprises a rotor integrally formed in the impeller means, the rotor having a plurality of permanent magnets circularly disposed therein such that polarities of the magnets alternate between north and south poles around the rotor.

22. A continuous flow pump for pumping sensitive biological fluids comprising:
    a construct having a first pump housing half and a second pump housing half hermetically sealed to the first pump housing half to form the construct, the construct having a hollow interior and an axial center;
    a pump inlet vessel formed from the first pump housing half and having an inlet throughbore for passage of fluids therethrough and into the hollow interior of the construct;
    a pump outlet vessel radially located from the axial center of the construct and formed from the first and second pump housing halves and having an outlet throughbore for passage of fluids therethrough from the hollow interior of the construct;
    an impeller means disposed within the hollow interior of the construct and out of contact therewith and having an impeller intake opening, impeller chambers, and impeller vanes having a spiral curvature for forming the impeller chambers, the impeller means for controlling fluid flow into the pump inlet vessel, through the hollow interior of the cavity, and out of the pump outlet vessel;
    a magnetic means for suspending the impeller means out of contact with the hollow interior of the construct and for selectively rotating the impeller means to thereby control fluid flowing through the continuous flow pump, said magnetic means providing control over five degrees of freedom of motion of the impeller means, including (i) one axial translational axis, (ii) two radial translational axes, and (iii) two rotational axes controlled for moment, wherein at least one of the five axes controlled for moment, axial translation, and radial translation is controlled by a set of electromagnetic actuators in the housing positioned to co-operate only with a corresponding set of non-permanently magnetized magnetic material in the impeller means; and
    a motor means for controlling rotational speed of the impeller means.

23. A method for pumping sensitive biological fluids using a pump comprising the steps of:
    selecting a pump device having an impeller magnetically suspended within a housing of the pump by means of electromagnetic actuators in the housing positioned to co-operate only with a corresponding set of non-permanently magnetized magnetic material in the impeller, the impeller having arcuately shaped vanes for reducing impact on the sensitive fluids traveling through the pump;
    positioning the impeller within the housing according to signals received from magnetic means that are used to magnetically suspend the impeller; and
    adjusting the impeller rotational speed and thus the rate of fluid flow according to signals received from an input and an output of the pump.

24. Apparatus of claim 19 wherein the acceleration forces are selected from the group including gyroscopic and gravitational forces.

* * * * *